(12) United States Patent
Dimitri et al.

(10) Patent No.: US 12,383,279 B2
(45) Date of Patent: Aug. 12, 2025

(54) MEDICAL PACKAGING

(71) Applicant: GARRDE PTY LTD, Brunswick East (AU)

(72) Inventors: Jay Dimitri, Brunswick East (AU); Mark Dimitri, Brunswick East (AU)

(73) Assignee: GARRDE PTY LTD, Brunswick East (AU)

(*) Notice: Subject to any disclaimer, the term of this patent is extended or adjusted under 35 U.S.C. 154(b) by 53 days.

(21) Appl. No.: 17/971,929

(22) Filed: Oct. 24, 2022

(65) Prior Publication Data

US 2023/0050830 A1    Feb. 16, 2023

Related U.S. Application Data

(63) Continuation of application No. PCT/AU2021/051243, filed on Oct. 26, 2021.

(51) Int. Cl.
| | |
|---|---|
| *A61B 50/30* | (2016.01) |
| *A61B 17/122* | (2006.01) |
| *A61B 17/3215* | (2006.01) |

(52) U.S. Cl.
CPC ...... *A61B 17/1222* (2013.01); *A61B 17/3215* (2013.01); *A61B 50/30* (2016.02)

(58) Field of Classification Search
CPC ............ A61B 17/3201; A61B 17/1222; A61B 17/3215; A61B 50/30
USPC ................................. 150/161, 154; 206/363
See application file for complete search history.

(56) References Cited

U.S. PATENT DOCUMENTS

| | | | | |
|---|---|---|---|---|
| 4,878,903 A | * | 11/1989 | Mueller | A61M 3/0262 |
| | | | | 604/199 |
| 7,866,468 B2 | * | 1/2011 | Kyritsis | A61B 50/20 |
| | | | | 206/363 |
| 8,137,332 B2 | * | 3/2012 | Pipelka | A61L 2/26 |
| | | | | 604/411 |
| 10,220,995 B2 | * | 3/2019 | Zacherle | B65D 75/563 |
| 2008/0202961 A1 | * | 8/2008 | Sharp | A61M 5/002 |
| | | | | 206/364 |
| 2009/0093757 A1 | * | 4/2009 | Tennican | A61J 1/2096 |
| | | | | 604/82 |

(Continued)

OTHER PUBLICATIONS

International Search Report with Written Opinion issued for International Patent Application No. PCT/AU2021/051243, mailed on Jan. 11, 2022.

*Primary Examiner* — Steven A. Reynolds
(74) *Attorney, Agent, or Firm* — Myers Wolin, LLC

(57) ABSTRACT

Medical packaging is provided for enclosing a single-use medical device with multiple frangible operating lines and corresponding frangible connections to define a removable first end which reveals at the time of use an operative part forming the key part that is to come into contact with the patient. The remaining part of the device including the controlling part is retained in the rest of the packaging but can be used to control the device without hindrance. Each of the multiple frangible operating lines indicating on the packaging the difference between the key part that forms the operating part of the device for one of a plurality of predefined medical procedures wherein the identification of the frangible operating lines immediately educates and instructs the user in the correct usage in a sterile and clean manner.

42 Claims, 11 Drawing Sheets

(56) References Cited

U.S. PATENT DOCUMENTS

| | | | | |
|---|---|---|---|---|
| 2009/0139889 A1* | 6/2009 | Kyritsis | ................. | A61B 50/30 |
| | | | | 206/439 |
| 2012/0061262 A1* | 3/2012 | Merboth | ................ | A61B 50/30 |
| | | | | 53/469 |
| 2012/0205269 A1* | 8/2012 | Ludvig | .................... | A61L 2/00 |
| | | | | 206/363 |
| 2013/0299373 A1* | 11/2013 | Johnson | ................. | B32B 27/18 |
| | | | | 428/339 |
| 2015/0374445 A1* | 12/2015 | Gombert | ............. | B25J 19/0075 |
| | | | | 606/130 |
| 2022/0338947 A1* | 10/2022 | Cancilla | ............. | A61B 17/1622 |

* cited by examiner

MEDICAL PACKAGING

CROSS REFERENCE TO RELATED APPLICATIONS

This application is a continuation of International Application No. PCT/AU2021/051243, filed Oct. 26, 2021, which takes priority from Australian Patent Application Nos. 2020903885, filed Oct. 27, 2020, and 2021221549, filed Aug. 24, 2021, the entire contents of each of which are incorporated by reference herein.

TECHNICAL FIELD

The present invention relates to medical packaging and in particular to medical packaging that holds a sterile single-use medical device for undertaking medical procedures. Medical procedures can be on human patients, animal patients or other biological procedures that would benefit from sterile or clean conditions.

BACKGROUND

The invention has been developed primarily for use in/with a medical packaging that holds a sterile single-use medical device and will be described hereinafter with reference to this application. However, it will be appreciated that the invention is not limited to this particular field of use.

The term "medical" throughout this document refers to any aspect of human or animal healthcare, occurring in human or animal hospital settings; clinical settings external to hospital such as general practices, veterinary practices, allied health practices, dentistry practices; first responder settings such as ambulance, fire rescue and wildlife rescue; personal settings such as home settings; aged care settings such as residential aged care facilities; and remote settings such as first-aid in the field. It further includes associated settings such as laboratories in which biological matter is handled, or other settings associated with the provision or investigation of healthcare.

Aseptic non-touch technique (ANTT) is a standardized approach to aseptic technique. The aim of aseptic non-touch technique is to minimize contamination of the patient by contact, droplet or airborne transmission of microorganisms from healthcare professionals, procedure equipment or the immediate environment, during invasive procedures. Aseptic non-touch technique has been shown to significantly improve the aseptic technique of healthcare workers. While aseptic non-touch technique has assisted to reduce healthcare associated infections (HAI), HAIs remain one of the most common, significant and preventable patient safety issues in the world today.

Currently, aseptic non-touch technique is the most used aseptic technique framework in healthcare and is rapidly evolving as a global standard. The core principles of aseptic non-touch technique are:
  Always decontaminate hands effectively;
  Never contaminate key parts of the equipment or the patients' susceptible site;
  Touch non key parts of the equipment with confidence; and
  Take appropriate infection prevention and control precautions.

The goal of the aseptic non-touch technique framework is asepsis. The term 'Asepsis' refers to an absence of microorganisms in sufficient quantity to cause infection. This is achievable in a typical healthcare setting.

In aseptic non-touch technique, maintaining an aseptic procedure is achieved by the fundamental concept and practical application of 'key part' and 'key site' protection. Key parts are the critical parts of medical devices that, if contaminated, provide a route for the transfer of microorganisms directly onto or into a patient. In intravenous therapy, key parts include any part of the equipment that comes into direct or indirect contact with the liquid infusion. Key sites are areas of skin penetration that provide a direct route for the transmission of microorganisms into the patient, such as skin wounds. Aseptic non-touch technique procedure requires key parts and key sites to be maintained in an aseptic state at all times during invasive procedures.

Asepsis can be medical or surgical. Medical asepsis refers to a "clean" technique which aims to minimize the contamination of microorganisms. In comparison, surgical asepsis is a "sterile" technique which aims to eliminate all microorganisms from an object or area during an invasive procedure. In the hospital environment, sterile technique is typically achieved in an operating suite with a laminar flow system.

As such, two different types of aseptic non-touch technique exist to achieve asepsis. 'Standard aseptic non-touch technique' is used to achieve medical asepsis and 'Surgical aseptic non-touch technique' is used to achieve surgical asepsis.

Standard aseptic non-touch technique employs hand cleaning, non-sterile gloves and a general aseptic field which is managed generally, that is, key parts are protected within individual micro critical aseptic fields and non-sterilised equipment may be placed in the aseptic field. Environmental risks need to be removed or avoided and working areas/surfaces cleaned and/or disinfected. Standard aseptic non-touch technique is used when carrying out a procedure that is technically simple, short in duration and involves small key sites and equipment with a small number of key parts. Standard aseptic non-touch technique is used for everyday medical procedures, including wound care, vaginal examination and use of intravenous devices.

Surgical aseptic non-touch technique employs a surgical hand scrub and sterile gloves. The sterile field is managed critically, meaning that only sterile equipment can come into contact with it and gloves must be kept sterile at all times. Surgical aseptic non-touch technique is used for technically complex long procedures that involve large open key sites and repetitive use of procedure equipment, including complex equipment with many key parts.

This present invention is intended to operate where standard aseptic non-touch technique is used to achieve medical asepsis in everyday medical procedures. The present invention is not intended to be used for surgical aseptic non-touch technique.

The present invention does not replace standard aseptic non-touch technique but facilitates its achievement and improves the standard of infection control able to be achieved in everyday medical procedures in a number of settings.

Healthcare associated infections are one of the most common, significant and preventable patient safety issues in the world today. Each year in Australia alone, over 180,000 patients suffer from healthcare associated infections caused by the transmission of microorganisms. This prolongs patient hospital stays and consumes in excess of 2 million hospital bed days per year.

Healthcare associated infections lead to increased use of antimicrobial drugs, primarily antibiotics. Microorganisms continue to adapt to the antimicrobial medications used in the healthcare environment, accelerating the development of antimicrobial resistance, resulting in non-treatable microorganisms that can present devastating risks to patients and public health.

10% of healthcare associated infections are caused by the airborne transmission of microorganisms. In addition to contact and droplet transmission, even COVID-19 has shown indoor airborne transmission. Outside of an operating suite, there are no techniques available to deal with the contamination of single-use medical devices by airborne transmission during use.

90% of healthcare associated infections are caused by contact transmission. There are approximately 3 million bacteria per square centimetre of skin, and there is no evidence that the use of hospital gloves reduces the incidence of cross-infection. Contrary to popular belief, gloves are worn to protect the user, not the patient, from hazardous substances such as bodily fluids.

Bacteria are always present on the skin of the hands and classified as either transient or resident bacteria. Transient bacteria are not usually present on the hand. These bacteria are acquired by contact with infectious patients or contaminated surfaces. Hence, healthcare settings are considered high-risk sites for cross-infection. Resident bacteria are deeply ingrained into the skin of the hand and cannot even be completely removed by thorough handwashing. The two main types are Staphylococcus Aureus and Staphylococcus Epidermidis, and both can cause severe and potentially fatal infections The avoidance of cross-contamination in a health environment is addressed by the use of sterile single-use medical devices. However, this by itself is not sufficient unless the sterile single-use medical device is used in accordance with aseptic technique.

Aseptic technique is a procedure used to prevent the transfer of pathogenic microorganisms to a susceptible site on the patient that may result in the development of infection. Currently, aseptic non-touch technique is the most used aseptic technique framework in healthcare and is rapidly evolving as a global standard. Standard aseptic non-touch technique procedure requires key parts to be maintained in an aseptic state at all times during invasive procedures.

The core principles of aseptic non-touch technique are:
Always decontaminate hands effectively
Never contaminate key parts of the equipment or the patient's susceptible site
Touch non key parts of the equipment with confidence
Take appropriate infection prevention and control precautions.

The goal of the aseptic non-touch technique framework is medical asepsis. Medical asepsis refers to a "clean" technique which aims to minimize cross-contamination by pathogenic microorganisms.

Despite current measures to achieve aseptic non-touch technique, healthcare associated infections continue to rise in incidence and prevalence around the world. The success and effectiveness of aseptic non-touch technique currently depends on a number of significant variables, including adherence to handwashing and aseptic non-touch technique procedures, the competency and discipline of healthcare practitioners and the availability of resources and infrastructure. Many countries have not even been able to adopt aseptic non-touch technique in healthcare settings due to numerous factors including deficient infrastructure; deficient training, compliance systems and sanitation; patient overcrowding and healthcare understaffing, as well as general attitudes of non-compliance by healthcare providers towards basic infection control procedures.

Medical devices can include a complex apparatus that is reused on many patients. If undertaking sterile practice is medically important then it can be that the whole device is covered by a replaceable disposable sterile covering. This is effective with devices that can only operate on a patient with indirect contact from within the covering. These devices and their complexity mean that they are not able to have the benefit of direct contact with the patient. The cost of disposing of the device after use is far too much and therefore the best use of the medical device is not achieved as it is not able in a broad range of environments acceptable to be in direct contact. To obtain the full benefit of direct contact, it is necessary for such complex and costly instruments to only be used in an expensive sterile surrounding of a hospital surgical room or the like and to be sterilized through hospital procedures in autoclaves.

However, a single-use medical device is a device where the key parts need to be in direct contact with the patient to perform the medical procedure. Therefore it is a single-use device and it is disposed of after its usage in the medical procedure. Merely being a single-use medical device is not sufficient as it can fail the sterile procedures as readily as for non-disposable medical devices. Adherence to aseptic protocols while using the device is required but is complex and depends on many variables as detailed above. It is therefore important to aid the use of single-use medical devices so as to improve the ability of the user to achieve medical asepsis through aseptic non-touch technique, and help avoid failing aseptic protocols.

Present packaging of single-use medical devices requires complete removal so the device can be revealed and directly contactable to the patient. In the prior art the packaging is generally in one of four forms of:

1. A rigid material casing that encloses the single-use medical device and needs to be unscrewed or broken in order for the device to be removed and thereby be usable;
2. A plastic wrapper that just encloses the single-use medical device and needs to be torn off in order for the device to be usable;
3. A tray having a shaped moulding forming a cavity that fits the outline of the single-use medical device and the tray is covered with a sheet layer which must be torn off in order for the device to be removed from the shaped cavity and thereby allow the single-use medical device to be usable;
4. A shrink wrap of the single-use medical device where the device is covered and heat is applied to shrink the wrap tightly around the medical device and requiring that the wrapping must be torn away in order for the device to be capable of being used.

These present forms of packaging are generally beneficial for allowing a sterile single-use medical device to be transported from place of manufacture to the medical transport means to the medical procedure location.

However further problems occur when the sterile single-use medical is fully released from its packaging, as the sterile environment benefits of the packaging are complete removed. Due to the complexities of the packaging, or the actual act of removing the device from the packaging, the user is required to directly handle the device such that there is obligatory cross-contamination between the user and the device. The device is also completely exposed to droplet and airborne cross-contamination by pathogenic microorganisms.

With present packaging, the sterile single-use medical device cannot be retained at least partially in its packaging as the medical practitioner is unable to effectively control the device as the packaging cannot be used that way. The packaging provides a hindrance and even acts counter to the control that the medical practitioner requires. This is particularly the case when the sterile single-use medical device has moving parts.

There are clearly many problems with present packaging—Present packaging must be removed and discarded—Presently in everyday procedures, sterile single-use devices need to be completely removed from packaging to be used. Therefore, the single-use medical device is completely exposed for an undefined amount of time, touched directly by the user, and placed directly onto non-sterile surfaces. The result is an obligatory loss of sterility of the device. The exposed device is susceptible to cross-contamination with pathogenic microorganisms via contact, droplet and airborne spread. These microorganisms can be directly transmitted to the patient's key site via the device and the consequences for the patient can be severe or fatal. Presently, even where aseptic non-touch technique principles are adhered to by the healthcare worker, the device is already contaminated and cannot be used in a sterile fashion.

Present packaging is wasteful—Presently in everyday procedures, packaging must be completely removed for the single-use medical device to be used. The packaging represents the best asset for maintaining the device's sterility, and yet is discarded before the device may be used. Once the medical device has been exposed for its function and handled directly, the device is susceptible to cross-contamination and no longer sterile. Aseptic non-touch technique aims to keep the device in a clean state for use. This involves use of secondary equipment that can include a trolley which must be cleaned with detergent and water, or disinfectant and single-use cloth; a portable dish such as a kidney dish which similarly must be cleaned with detergent and water, or disinfectant and single-use cloth; and single-use dressing packs which comprise plastic trays, plastic tweezers, gauze swabs and plastic drapes. Healthcare workers often call on extra staff to assist the procedure, in order to facilitate adherence to the complex infection control protocols of aseptic non-touch technique. The reliance of present medical packaging on secondary resources and equipment multiplies the waste associated with the singular use of a medical device.

Cross-contamination with antimicrobial resistant organisms—The World Health Organisation has declared that antimicrobial resistance to be one of the top ten global public health threats facing humanity. Antimicrobial resistance has lead to the development of non-treatable pathogenic microorganisms. Cross-contamination of patients by healthcare workers with antimicrobial resistant organisms can lead to severe or fatal infection. The rise in antimicrobial resistant organisms, in conjunction with the Covid-19 pandemic, has lead to a renewed global focus on infection control. However, single-use medical devices still continue to be fully exposed for their use and continue to be at significant risk of cross-contamination via contact, droplet and airborne transmission. These devices can transmit these pathogenic microorganisms directly onto the key site on a patient. Such a contamination risk is incongruent with today's increased focus on stringent infection control.

Difficulty during urgent or emergent situations in Hospitals—Urgent or emergent situations, even in hospitals, are extremely challenging situations. In these situations, the patient is at risk of losing life or limb. Therefore, priority is given to the performance of critical treatment measures, usually under extreme pressure and time pressure. In such situations, studies have shown that healthcare workers are often unable to adhere to the demands of aseptic non-touch technique, despite best efforts. For example, healthcare workers are unable to constantly pause procedures for handwashing/drying breaks during a critical emergency. Medical studies in this area have shown that patients are prone to acquire serious or fatal infections due to contamination of exposed single-use medical devices with pathogenic microorganisms on the glove of the healthcare worker. The consequences of such infection are severe or fatal, particularly if the patient being treated is in a critical condition.

Difficulty in the field—Urgent or emergent situations in the field are much more difficult to manage than similar situations in the controlled environment of a hospital. Once present packaging is fully removed from a single-use medical device to expose it for use, aseptic non-touch technique is required to maintain device cleanliness. However, the success of aseptic non-touch technique is premised on the ability of the healthcare worker to effectively avoid or remove environmental contaminants and wash their hands. This is often impossible in the first responder scenario in the field.

For example, consider use of a syringe on a beach by a first responder. The syringe must be completely exposed in order for medications to be drawn up and then dispensed to the patient. Particulates such as sand, which can be contaminated with pathogenic microorganisms, can infiltrate the syringe and its contents, as it lays completely exposed during the drawing up and preparation process. The drawing up and preparation process may be interrupted or prolonged in rapidly changing and unpredictable circumstances, increasing the exposure time and cross-contamination risk of the syringe.

Secondary equipment such as trolleys, dishes and trays may not be available. The first responder may be alone or with one other partner, forcing the first responder to place the syringe on unsterile or unclean surfaces while managing the patient. Under duress, the healthcare worker may pull the plunger too far back, exposing the rubber stopper, allowing direct contamination of the inside of the barrel and its contents with pathogenic microorganisms and liquid or solid debris. In a demanding scenario, a single-use syringe may be used more than once to dispense medications, increasing the risk of plunger cross-contamination with pathogenic microorganisms. In the urgent scenario, the healthcare worker is unable to pause multiple times to wash hands and change gloves. The barriers to performing aseptic non-touch technique in the field are numerous, leaving the exposed single-use device completely susceptible to cross-contamination.

Difficulty in resource scarce countries—Once present packaging is fully removed from a single-use medical device to expose it for use, aseptic non-touch technique is required to maintain device cleanliness. However, there are a number of significant barriers to the achievement of aseptic non-touch technique principles in resource scarce countries. Barriers include deficient infrastructure such as water storage and dispensing systems; deficient training; poor sanitation; poor compliance systems; patient overcrowding; healthcare understaffing; general attitudes of non-compliance by healthcare providers towards basic infection control procedures; deficient resources such as hand sanitiser or soap; deficient secondary equipment such as trolleys; and water scarcity or systemic contamination of water supplies.

Magnifying these barriers is the higher rate of antimicrobial resistant organisms in resource scarce countries and the often inappropriate re-use of single-use medical devices by healthcare workers. Present packaging, once fully removed from a single-use medical device, leaves the device completely exposed for undefined periods of time. With deficient critical resources, aseptic non-touch technique principles cannot be implemented to protect single-use medical devices from cross-contamination in resource scarce countries.

General attitudes of non-compliance with infection control—Once present packaging is fully removed from a single-use medical device to expose it for use, aseptic non-touch technique is required to maintain device cleanliness. Aseptic non-touch technique is wholly reliant on the healthcare worker effectively performing hand hygiene. However, in developed countries, health-care worker adherence to recommended hand hygiene practices remains unacceptably low and average compliance with hand hygiene recommendations is usually estimated as <50%.

Several barriers to hand hygiene are reported by healthcare workers and include skin breakdown and irritation; interference with worker-patient relation; patient needs perceived as priority; forgetfulness; ignorance of guidelines; insufficient time, high workload and understaffing; lack of scientific information demonstrating impact of improved hand hygiene on hospital infection rates; inconveniently located or insufficient numbers of sinks; low risk for acquiring infection from patients; belief that glove use obviates need for hand hygiene; and ignorance of or disagreement with guidelines and protocols. Despite major pushes for improved hand hygiene, no single intervention has consistently improved hand hygiene compliance. Single-use medical devices, once fully exposed, are fully susceptible to cross-contamination from unclean hands and can directly transmit pathogenic microorganisms to the key site on a patient.

Presently, aseptic non-touch technique requires extensive training and experience. Once present packaging is fully removed from a single-use medical device to expose it for use, aseptic non-touch technique is required to maintain device cleanliness. Aseptic non-touch technique is a medical procedure that requires extensive training, secondary equipment and resources, and experience through repetition and competency assessments. Core competencies that must be mastered include effective hand cleaning using a systematic method, correct glove use, key part and key site identification and protection, skillful non-touch technique, key part disinfection and aseptic field management, if aseptic non-touch technique is to be effective in minimizing contamination of a single-use medical device by pathogenic microorganisms. Persons who are not medically trained are unable to perform aseptic non-touch technique. Presently, this means that procedures performed outside of hospital by a member of the public, such as use of diabetic needles in the home environment or use of a first aid kit in a public space, will fail basic infection control mandates. The resulting unclean procedure places the treatment receiver at significant risk of infection, from cross-contamination with contact, droplet or airborne pathogenic microorganisms.

No protection from droplet or airborne spread—Presently in everyday procedures, medical packaging for sterile single-use medical devices needs to be completely removed to allow its use. Aseptic non-touch technique principles only help to minimise contamination by contact transmission. However, as the device is completely exposed, aseptic non-touch technique principles cannot protect the device from droplet or airborne contamination. There is no protection of the device from droplet or airborne spread outside of an operating suite. In situations where medical devices need to be prepared prior to contact with the patient, there is a significant amount of time that the device is exposed and prone to droplet or airborne contamination. Avoidance of such cross-contamination is critical, particularly given the rising prevalence of antimicrobial resistant organisms and the droplet/airborne spread of the COVID-19 virus amidst the current pandemic.

Contamination of plunger, barrel and syringe contents—With sterile single-use syringes, as the plunger of a syringe moves up and down, it directly contacts internal surfaces of the syringe barrel. Any microorganisms transmitted to the sides of a syringe plunger by finger contact while withdrawing the plunger, or from the immediate environment, can therefore be transferred to the inside of the barrel, and then directly to the syringe contents. This is particularly the case if the plunger is drawn in and out more than one time. Contaminants within the barrel of the syringe and syringe contents would then be dispensed directly onto a key site of the patient, potentially causing severe or fatal infection.

Difficulty with syringe pumps—With sterile single-use syringes, another common scenario using the syringe with a syringe pump, which is a portable battery-operated pump that can be used to achieve continuous subcutaneous administration of drugs. These pumps can be used in several situations, as an alternative to oral medication administration. Syringe pumps can also be used outside of the perfect location of a hospital such as in nursing homes and private residences. The syringe is attached to the syringe pump and can be left for periods up to 24 hours, with the plunger extended and completely exposed in an unsterilized environment. In these situations, there is an extended period of time in which pathogenic microorganisms may contaminate the plunger and the barrel and syringe contents.

Contamination with hazardous drugs—With sterile single-use syringes, using the syringes to draw up and prepare hazardous drugs such as cytotoxic agents, medical studies have shown that syringe plungers can themselves be contaminated by hazardous drugs under routine drug preparation conditions. The exposed syringe then becomes a significant route of exposure to hazardous drugs that can contaminate an entire work area. Such a contamination event is extremely serious, potentially harming pharmacy personnel and nurses, as well as patients and their families.

It can be seen that known prior art methods and apparatuses of medical packaging that hold a sterile single-use medical device has the problems of:

a) A sterile single-use medical device being unpackaged and the package being discarded to allow the device to be used and therefore the sterile single-use medical device is directly touched, placed directly on surfaces, and exposed to contact, droplet and airborne microorganisms that void the sterile nature of the single-use medical device.

b) Not allowing versatility in use of sterile single-use medical devices while retaining a sterile environment.

c) Requiring training, experience and secondary procedures to retain location and sterile single-use medical devices in sterile conditions according to multiple protocols.

d) Losing advantage of sterile single-use medical packaging.

e) Lack of ease of use of sterile single-use medical equipment according to aseptic non-touch technique principles to achieve medical asepsis.

f) No protection of a single-use medical device from airborne transmission of microorganisms as the device is completely exposed in order to be used.

g) Lack of minimization of contact, droplet and airborne transmission of microorganisms to patients during the use of single-use medical devices in healthcare settings.

h) If hand-washing is not available or not performed, a sterile single-use medical device fully exposed is easily contaminated posing substantial risk of cross-contamination.

i) No protection of a single-use medical device from contamination during use if there are visible solid or liquid contaminants.

j) Obligatory loss of sterility when a single-use medical device is used in the absence of a surgical aseptic method.

k) Lack of protection of the plunger shaft of a sterile single-use syringe during use which can lead to cross-contamination of the contents and severe or fatal infections such as bacteraemia in the patient.

l) Reliance on secondary resources and equipment multiplies the waste associated with the singular use of a medical device.

m) Requiring the device to be fully exposed for use making the device susceptible to cross-contamination by airborne and droplet antimicrobial resistant organisms.

n) Difficulty using sterile single-use medical devices according to aseptic non-touch technique principles during urgent or emergent situations in hospitals.

o) Difficulty using sterile single-use medical devices according to aseptic non-touch technique principles during urgent or emergent situations in the field.

p) Difficulty using sterile single-use medical devices according to aseptic non-touch technique principles in resource scarce countries.

q) Potential contamination of the sterile single-use syringe plunger with hazardous drugs and exposure of workplace or persons to these hazardous drugs.

r) Significant potential for human error given complexity of procedures required to use a fully exposed sterile single-use medical device according to aseptic non-touch technique principles.

s) Difficulty monitoring compliance with aseptic non-touch technique principles.

It can be seen that a localized sterile environment is needed when use of single-use sterile equipment is not in a controllable environment. This can be in private residence or in the field or in external locations where resources are not available. It is therefore important that a system is needed for other than the perfect location such as a hospital. A system is also needed if the user does not have training or experience with aseptic non-touch technique.

The present invention seeks to provide medical packaging that holds a sterile single-use medical device which will overcome or substantially ameliorate at least one or more of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY

According to a first aspect of the present invention, there is provided A medical packaging for holding a sterile single-use medical device, wherein the medical device has at least one operative part which in use is a key part for direct contact to a patient and further has at least one controlling part for controlling the at least one operative part. The packaging includes a body forming an enclosing volume able to hold a single-use medical device in a sterile condition, the body having at least one first end portion, at least one second portion and at least one openable connection between the at least one first end portion and the at least one second portion to allow the at least one first end portion to be disconnected from the at least one second portion.

The at least one first end portion is sized and shaped for substantially covering an operative part of the single-use medical device.

The at least part of the at least one second portion is sized and shaped for substantially covering a controlling part of the single-use medical device.

The at least one openable element is able to have the at least one first end portion displaced into an open state at time of use to allow the at least one operative part of the single-use medical device to be revealed and usable directly on the patient.

The at least one second portion remains and allows the at least part of the at least one second portion be controlled by the at least one controlling part while the at least one controlling part remains substantially within the at least one second portion.

Embodiments of the present invention may maximize the effectiveness of the main principles of aseptic non-touch technique which are:

Always decontaminate hands effectively

Never contaminate key parts of the equipment or the patient's susceptible site

Touch non key parts of the equipment with confidence

Take appropriate infection prevention and control precautions where key part means the part of a device which comes into direct contact with a patient, or an injection port and therefore must remain free from cross-contamination.

Embodiments of the present invention can be said to readily:

a) identify the key parts of the sterile single-use medical device which should never be touched b) serve as a visual and physical indicator to the user differentiating the key parts and non-key parts of the device c) allow only the covering over the operative part to be readily removed without contacting the operative part d) Reduce the time the operative part is exposed before use e) Retain the covering over the controlling part and other non-operative part to be still on the device while using the operative part of the device.

The medical packaging can hold a sterile single-use medical device. It includes a body forming an enclosing volume with at least one first end portion and at least one second portion that can be an end portion or central portion and together is able to hold the single-use medical device therein in a sterile condition, with the at least one first end portion sized and shaped for substantially covering an operative part of the single-use medical device, and the at least one second portion sized and shaped for substantially covering a controlling part of the single-use medical device.

There can be at least one openable element on at least part of the at least one first end portion wherein the openable element on at least part of the at least one first end portion is able to be substantially displaced into an open state at time of use to allow operative part of the single-use medical device to be used while the controlling part remains substantially within the second portion.

It can be seen that embodiments of the invention of medical packaging provides the benefit of achieving a single-use only sterile sealed packaging, used to enclose a single-use medical device, enabling the user to hold and use the enclosed device without directly touching it, and thereby minimizing potential for contamination of the device by microorganisms via contact, droplet and airborne transmission.

In particular the controlling part of the sterile single-use medical device can be held due to the flexibility and texture of the at least one second portion allowing the user to have full control of the single-use medical device without touching the device to fully remove it from the packaging. By this novel packaging the operative part of the device has been released and is maintained in a sterile localized area for application to the patient and the device is not touched by the user but fully controllable by being held by the user while still substantially within the sterile packaging.

Therefore, the system is fully transportable for use in a location other than the perfect location of a hospital.

According to a further embodiment of the present invention, there is provided a medical packaging that holds a sterile single-use medical device wherein the medical packaging has at least one first end portion which corresponds in size and shape to an operative part of the single-use medical device.

According to a still further embodiment of the present invention, the medical packaging can hold a sterile single-use medical device and the medical packaging has at least one second portion which corresponds in size and shape to a controlling part of the single-use medical device.

It can be seen that embodiments of the invention of medical packaging provides the benefit of allowing the single-use medical device to be used while remaining substantially within the sterile packaging. However, as the device has movable parts it is important that one or other or both of the first end portions and second portions have movable or shaped parts which allow the movement of the operative parts or controlling parts or both of the single-use medical device while remaining substantially within the sterile medical packaging. However again by this novel packaging the operative part of the device has not been released until just before use and thereby is maintained in a sterile localized area for application to the patient and the single-use medical device is not touched by the user but fully controllable by being held by the user while still substantially within the sterile packaging.

According to another embodiment of the present invention, there is provided a medical packaging that holds a sterile single-use medical device and has at least one part which transforms in a corresponding manner to the change of shape of an operative part of the single-use medical device. With such medical packaging able to transform to accommodate the single-use medical device which operatively changes dimensions in its use then the single-use medical device can still stay substantially within the packaging and be fully operative. By this novel packaging the operative part of the device has been released and is maintained in a sterile localized area for application to the patient and the device is not touched by the user but fully controllable by being held by the user while still substantially within the sterile packaging.

Embodiments of the invention allow for packaging and use of shaped movable single-use medical devices. The packaging allows for holding in a sterile condition and usage of single-use medical devices that require operative parts to move relative to each other to form an operative end or require controlling parts to move relative to each other to form a controlling end or a combination thereof. The shaped movable packaging can hold such single-use medical device and allow them to be operatively moved while still substantially in the packaging.

Embodiments of the invention can further provide for packaging and operative use in sterile conditions of change of shape or other transformations of single-use medical devices while still remaining substantially in the packaging by use of an intermediate second portion which can be an expandable concertina portion that allows for retaining a sterile outer protection over a range of lengths of the single-use medical device such as in the form of a syringe.

Embodiments of the invention also provides for packaging and operative use in sterile conditions of multi ended operative single-use medical devices that have a packaging with a plurality of first end portions connected to a second portion that extends and connects therebetween and forms a second central portion. In this way there is selective use of one or more operative parts while still being held by the controlling part that remains in the central second portion and thereby ensures contactless use. And also keeps sterile other first end portions which are not in operation, during use of another first end portion.

In one form, embodiments of the invention provide a medical packaging including single-use only sterile sealed package with openable elements, used to enclose a single-use medical device. By activating an openable element and removing a small section of the package, the enclosed device can be exposed for its function without any direct touching of the device, and the device is held and used through the remainder of the packaging which remains around the device at all times, without any direct touching of the device by the user.

In another form embodiments of the invention provide a medical packaging that holds a sterile single-use medical device comprising a body forming an enclosing volume with at least one first end portion and at least one second portion able to hold the single-use medical device therein in a sterile condition wherein the at least one first end portion is sized and shaped for substantially covering an operative part of the single-use medical device. The at least one second portion is sized and shaped for substantially covering a controlling part of the single-use medical device; and at least one openable element on at least part of the at least one first end portion wherein the openable element on at least part of the at least one first end portion is able to be displaced into an open state at time of use to allow the at least one operative part of the single-use medical device to be usable and controlled by the at least one controlling part while the at least one controlling part remains substantially within the at least one second portion.

As the device is not touched directly by the user, this minimizes contamination of the device, therefore minimizing the transmission of microorganisms to the patient in the healthcare setting, and to the individual in the external location, in a fast, simple, reliable and straight-forward manner; wherein the medical packaging can provide improvements including any one or more of the following:

i. Improvements in structure and packaging of single-use medical devices in a sterile manner;

ii. Improvements in minimizing the transmission of pathogenic microorganisms to patients during the use of sterile single-use medical devices in healthcare settings or in the external location;
iii. Ability to minimize droplet and airborne transmission of pathogenic microorganisms during use;
iv. Improvements in using of single-use medical devices in a sterile manner;
v. Reducing need for secondary protocols due to eliminating of voiding actions which break sterile conditions of the device in the package;
vi. Reducing equipment resource burden;
vii. Reducing waste burden;
viii. Reducing need for assistant staff;
ix. Reducing risk of human error in upholding the aseptic non-touch technique principles;
x. Ability to ensure compliance with aseptic non-touch technique principles;
xi. Ability to uphold aseptic non-touch technique principles irrespective of the environment, raising the level of cleanliness achievable in locations external to hospital such as homecare settings and locations with deficient infrastructure and resources;
xii. Ability to retain a localized sterile location;
xiii. Ability to use the single-use medical device while substantially within the sterile packaging;
xiv. Ability to use the sterile single-use medical device without directly touching it to remove it from the packaging;
xv. Ability to use the sterile single-use medical device such as a syringe without placing it on a non-sterile surface in order to be usable in other than the perfect location of a hospital while maintaining sterile effectiveness;
xvi. Ability to use the single-use medical device without directly touching it or exposing it to contact transmission of microorganisms;
xvii. Ability to use the single-use medical device in a sterile fashion without requiring medical training or experience;
xviii. Retains advantage of sterile single-use medical packaging;
xix. Protection of substantial portion of the single-use medical device from droplet and airborne transmission of microorganisms during use;
xx. Protection of substantial portion of the single-use medical device from contamination by visible solid or liquid contaminants during use;
xxi. Ability to use the single-use medical device in the absence of surgical aseptic method without loss of sterility.
xxii. Ability for packaging to act as a visual and physical indicator during use, assisting the user to differentiate between key parts and non-key parts and to avoid contact with key parts.
xxiii. Ability for the user to choose how much of an operative part is revealed, minimizing unnecessary exposure of the device, therefore minimizing potential for cross-contamination by pathogenic microorganisms.
xxiv. Facilitates minimization of the amount of time a key part is exposed for a medical procedure, therefore minimizing potential for cross-contamination by pathogenic microorganisms.
xxv. Ability to reduce reliance on secondary resources, equipment and assistant staff.
xxvi. Reduces volume of waste.
xxvii. Facilitates aseptic non-touch technique in urgent or emergent situations.
xxviii. Facilitates aseptic non-touch technique in the field.
xxix. Facilitates aseptic non-touch technique in resource scarce countries.
xxx. Protects plunger of a sterile single-use syringe from contact, droplet and airborne contamination by pathogenic microorganisms as well as liquid or solid debris.
xxxi. Prevents contamination of workplace or persons from single-use syringe which has been contaminated by hazardous drugs.
xxxii. Improvements in compliance and compliance monitoring of aseptic non-touch technique.

It can be seen that embodiments of the present invention of medical packaging provides the benefit of a physical barrier substantially covering a sterile single-use medical device during its use, protecting against contact, droplet and airborne transmission of microorganisms.

It can be seen that embodiments of the present invention of medical packaging that holds a sterile single-use medical device is not intended to be used for surgical aseptic non-touch technique, but provides the benefit of an easier and more effective way to uphold standard aseptic non-touch technique to achieve medical asepsis, minimizing potential for cross-contamination of the device by pathogenic microorganisms in every day procedures and raising the standard of cleanliness achievable in those procedures.

It can be seen that embodiments of the invention of medical packaging that holds a sterile single-use medical device provides the benefit of easier working conditions for users and safer treatment conditions for patients that need sterile single-use medical devices.

It can be seen that embodiments of the present invention of medical packaging that holds a sterile single-use medical device provides a means of maintaining sterile or clean conditions external to the perfect location of a hospital such as homecare settings and locations with deficient infrastructure and resources Other aspects of the invention are also disclosed.

BRIEF DESCRIPTION OF THE DRAWINGS

Notwithstanding any other forms which can fall within the scope of the present invention, preferred embodiments of various different forms of the invention will now be described, by way of example only, with reference to the accompanying drawings in which.

DETAILED DESCRIPTION

Figure 1:
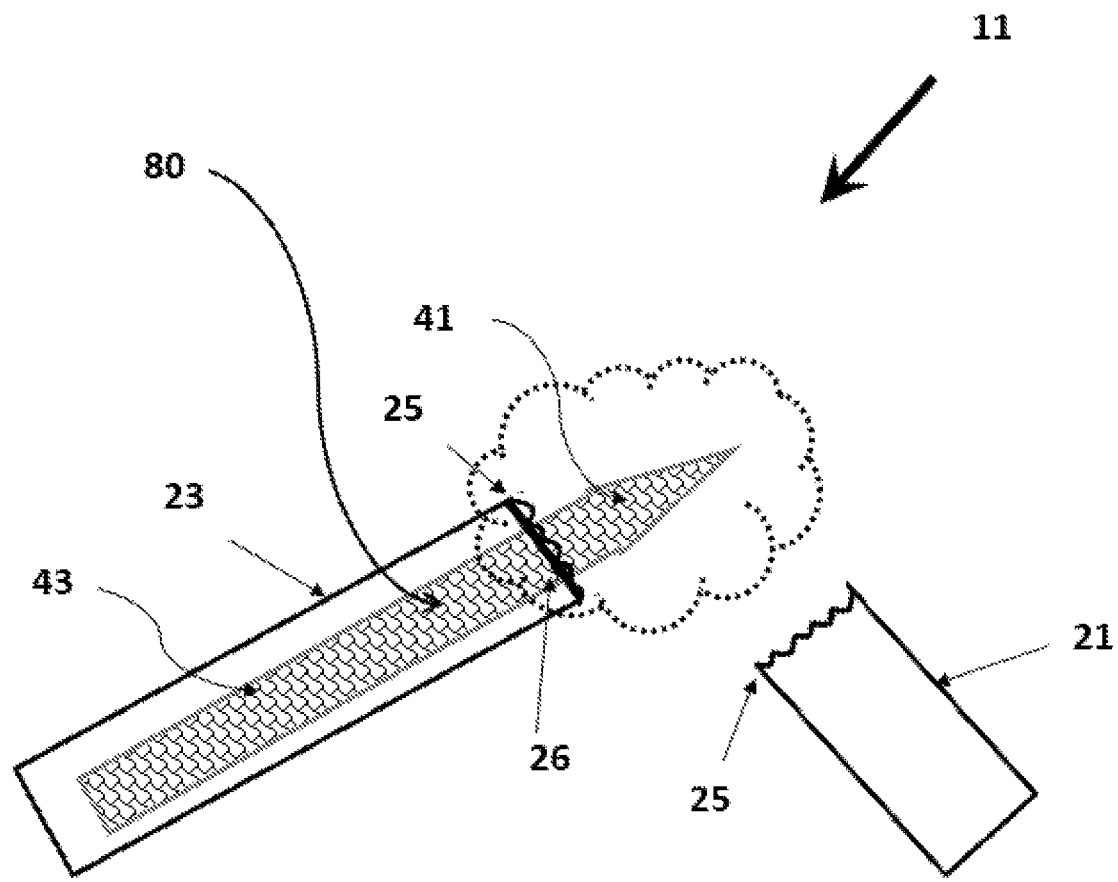
FIG. 1 is a diagrammatic view of a medical packaging that holds a sterile single-use medical device in accordance with a general preferred embodiment of the present invention having a first end portion and a second end portion intermediate with a frangible connection therebetween and a single frangible operating line identifying the key part of the device.

It should be noted in the following description that like or the same reference numerals in different embodiments denote the same or similar features.

Referring to the drawings there is shown a medical packaging 11, to 19 that holds a sterile single-use medical device 80 such as scalpel 81, cotton buds 82, thumb forceps or tweezers 83, scissors 84, syringe 85, vaginal speculum 86 and caliper and rule 87. There is also packaging 90 for a sterile rest box 88. This list is not limited but would be understood to include other single use devices such as ring forceps, suture blades, medication cups, clamps, and cannulas. Various embodiments shown in FIGS. 2 to 10 will be described later.

As shown conceptually in FIG. 1, embodiments of the invention provide a single-use only sterile package 11 with frangible connections 25, used to enclose a single-use medical device 80, 81 to 88.

The device 80 has an operative part 41 which is the part that is to come into contact with the patient and therefore needs to be revealed. However, the operative end of the single-use medical device 80 only needs to be revealed at the time, when it is actually to be used to contact the patient.

In this regard the medical packaging includes a first frangible operating line 26 that indicates on the packaging the difference between the key part that forms the operating part 41 of the device and can be in contact with the patient and should not be in contact with anything or anyone else to maintain the sterile and clean condition which means above normal environmental conditions to medical asepsis conditions. The identification of the first frangible operating line 26 immediately educates and instructs the user in the correct usage.

By activating the frangible connection 25 and removing a small section of the package being a first end portion 21, the enclosed device can be exposed minimally for its function without any direct touching of the device. The device is held and used through the remainder of the packaging of the second portion 23 which remains around the device 80 at all times, without any direct touching of the device by the user.

The single use medical device 80 has a controlling portion 43 which can be at the other end of the single-use medical device and therefore be a second end portion for the user to control the use of the operative part 41. However, this controlling portion can be at a central location and therefore be a controlling central portion.

As the device is not touched directly by the user, this minimizes contamination of the device, therefore minimizing the transmission of microorganisms to the patient in the healthcare setting, and to the individual in the external location, in a fast, simple, reliable and straight-forward manner.

The packaging allows the single-use medical device 80 to remain enclosed in the sterile packaging until just before use and therefore provides a sterile environment around the operative part 41 even at the time of use since the device has not needed to be taken out of the packaging but can be held while still substantially in the packaging and the operative part has a minimal time in open environment and generally its sterile environment lingers.

The medical packaging can also include parts that allow the packaging to be transformable without hindrance for controlling the medical device while the controlling part remains in the rest of the packaging.

Therefore, the packaging provides the results by one or more of:
  a) Holding of controlling part while still in packaging
  b) Ease of removal of first end portion
  c) No need to remove single-use medical device from packaging and therefore touch single-use medical device or place it down on a surface to be ready for use
  d) Ability to only reveal operative part at the last moment
  e) Ability to control operation while still substantially in the packaging.
  f) Ability to allow movement of the controlling part while in the packaging.

Figure 2:
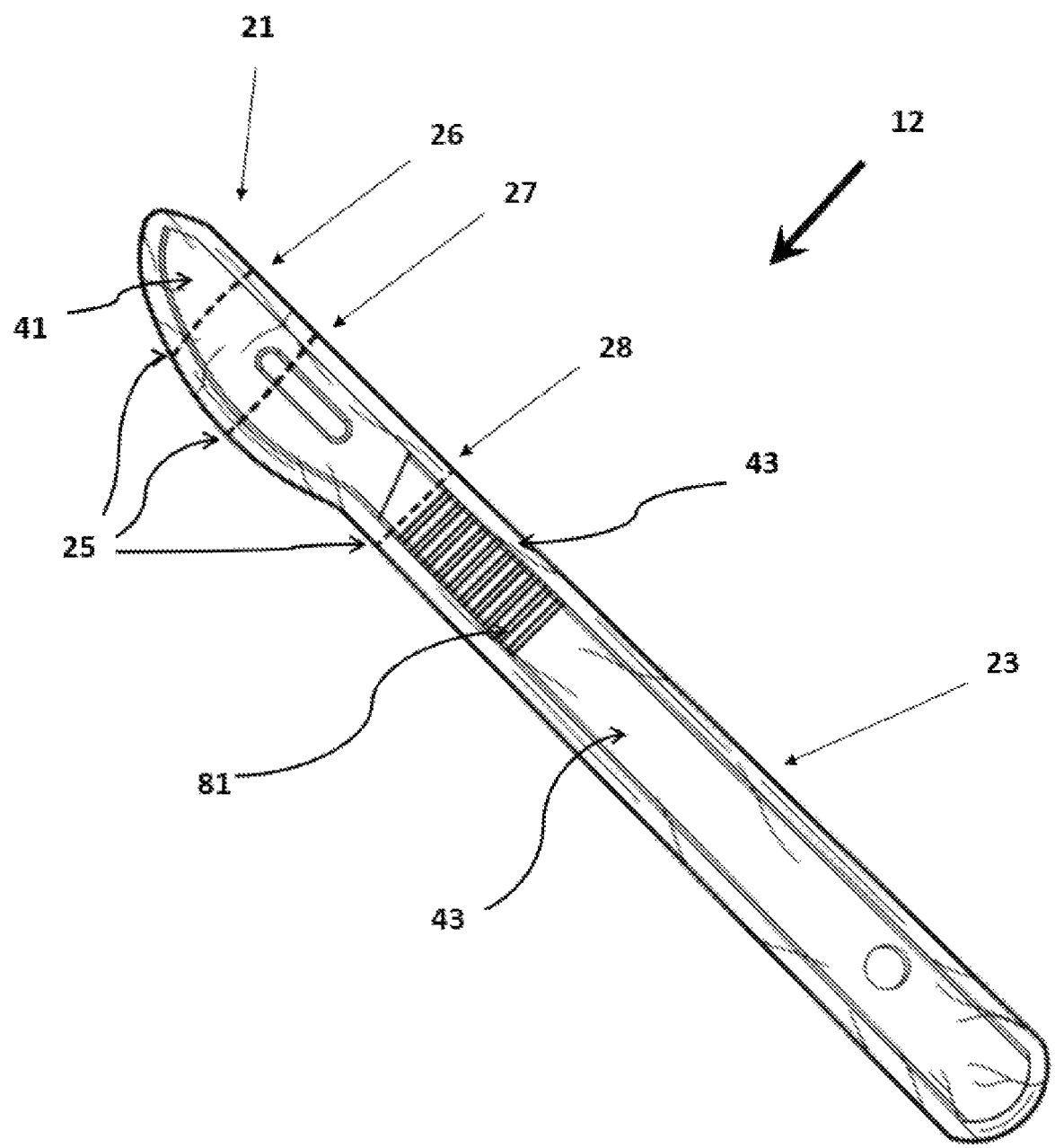
FIG. 2 is a diagrammatic view of a medical packaging that holds a sterile single-use medical device in the form of a scalpel having a first end portion and a second end portion intermediate with a frangible connection therebetween and multiple frangible operating lines identifying the key part of the device in accordance with another preferred embodiment of the present invention.
Figure 3:
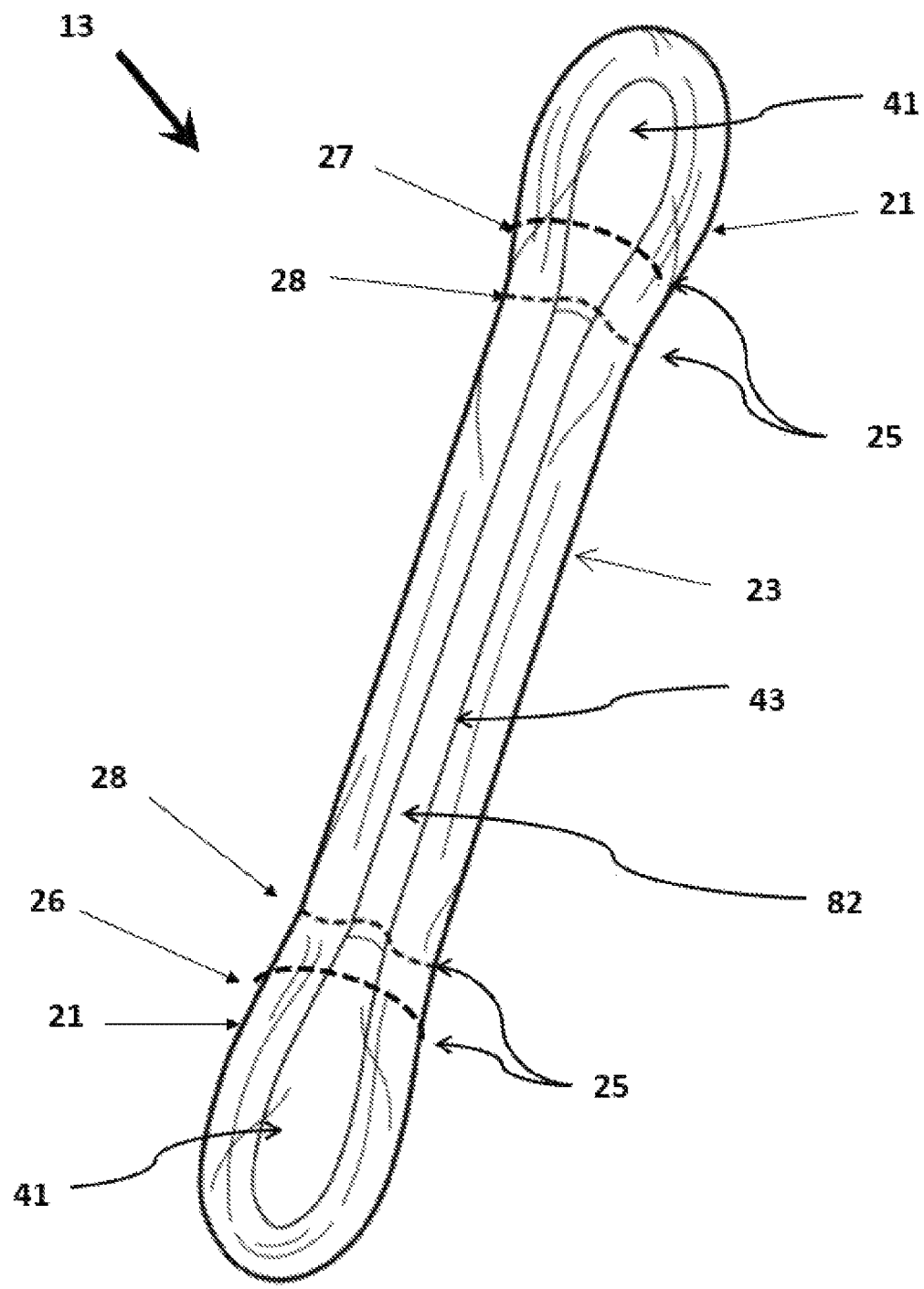
FIG. 3 is a diagrammatic view of a medical packaging that holds a sterile single-use medical device in the form of a double ended cotton bud that can be used as an applicator bud or an insertion swab in accordance with another preferred embodiment of the present invention having two first end portions and an intermediate central second portion therebetween.
Figure 4:
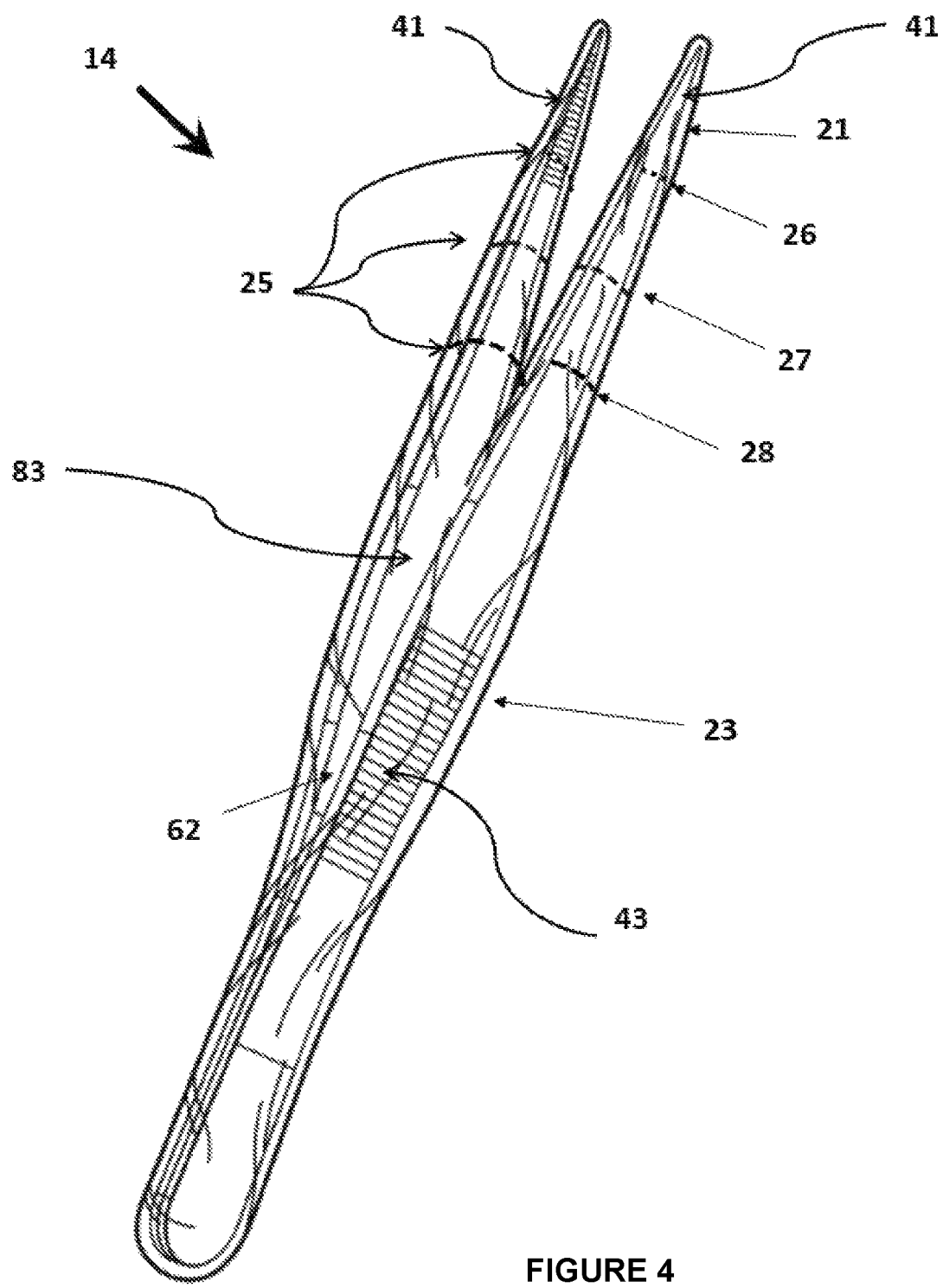
FIG. 4 is a diagrammatic view of a medical packaging that holds a sterile single-use medical device in the form of a set of tweezers that can be used in a plurality of ways at a plurality of inserted depths in the patient and in accordance with another preferred embodiment of the present invention having a plurality of frangible operating lines identifying the key part of the device and having openable connections at those lines so that a selected first end portion can be removed to show the relevant key part for the relevant selected medical procedure.
Figure 5:
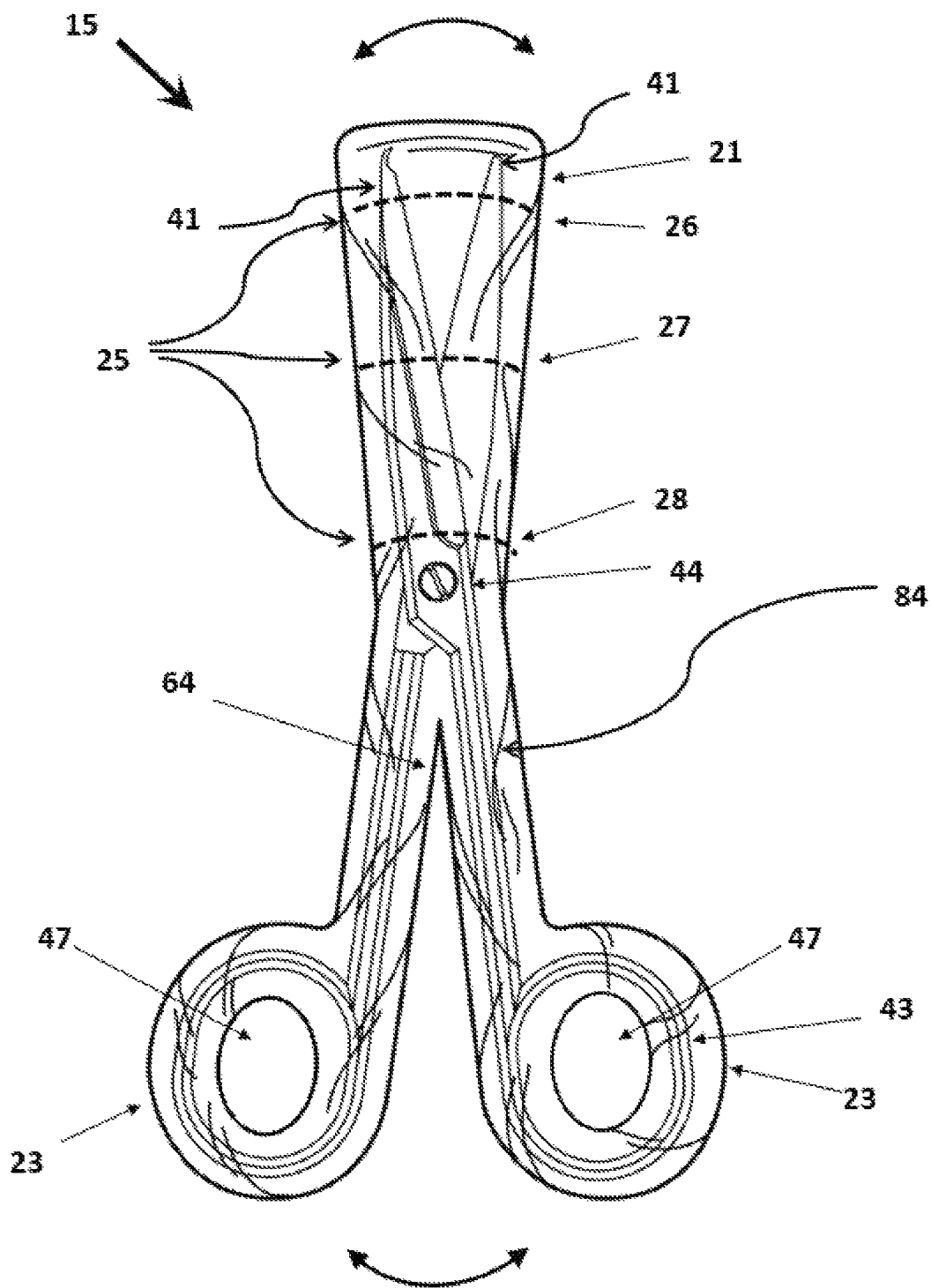
FIG. 5 is a diagrammatic view of a medical packaging that holds a sterile single-use medical device in the form of a set of scissors in accordance with another preferred embodiment of the present invention having a frangible operating lines identifying the key part of the device and having openable connections at that line so that a selected first end portion can be removed to show the relevant key part for the relevant selected medical procedure and the medical packaging being transformable by allowing pivoting action initiated by user with finger control in the controlling finger holes while still in the second portion of the packaging.

It can be seen that there are various forms of the invention shown in FIGS. 2 to 10, with novelty over each other including:
  a) Shaped fixed packaging such as in FIGS. 2 and 3 for holding a fixed shaped single-use fixed medical device 81, 82 that can be operatively used while still substantially in the packaging and where there is at least one frangible operating for use to indicate the key part in various predetermined medical procedures with the single use medical device and thereby various length of first end portion will be removed dependent on selected use
  b) Shaped Movable packaging such as in FIGS. 4 and 5 for holding a movable shaped single-use medical device that can be operatively moved while still substantially in the packaging and where there is at least one frangible operating for use to indicate the key part in various predetermined medical procedures with the single use medical device and thereby various length of first end portion will be removed dependent on selected use.
  c) Transformable Shaped Packaging such as in FIGS. 4 to 9 for holding a transformable shaped single-use medical device 83 to 87 that can be operatively moved while still substantially in the transformed packaging and where there is at least one frangible operating for use to indicate the key part in various predetermined medical procedures with the single use medical device and thereby various length of first end portion will be removed dependent on selected use There are a number of concepts of the novelty and inventiveness of the present packaging that are included individually or in a synergistic combination and details of those concepts are explained herein.

Openable with Partial Retention of Covering

The single use medical device could have the packaging simply removed. However then the user would be contacting the medical device at least next to the key part of the device and accidental contact or cross contamination from the user to the key part is highly likely.

The outside of the one or more second portions of the body of the packaging of the single use medical device is located in specific closeness to the non-key parts of the device and usually impossible to come into contact with the revealed open key part of the device. Therefore the user touching a surface away from and unable to contact the key part will ensure a higher likelihood of clean and sterile environment.

Indicator

The knowledge and understanding of what is the key part of a medical device is extremely important in order to ensure that the key part—being the part that is to come into contact with the patient—is retained as clean and sterile as possible. That is the key part should not be touched and it should not be laid on a surface such that cross contamination to the key part and to the patient in use will occur.

Without knowing which part or how much of the medical device is the key part there is a high likelihood that a non-qualified medical person will unwrap, accidentally touch or lay the device on a surface ready for the user to undertake the medical procedure. By these unthinking but intentionally helpful approach, the whole benefit of sterile packaging of the medical device is lost.

Even a trained medical person at the time of an urgent procedure and particularly in an emergency first aid situation which could be in less than optimum physical location needs assistance.

The packaging of embodiments of the present invention provides assistance in retaining a clean and sterile environment by providing a frangible operating line 26 substantially overlying the end of the key part. Therefore the identity of the key part is understood when still fully in the packaging by the frangible operating line 26. Furthermore the key part is still understood when the first end portion 21 that ends at the frangible operating line 26 is removed as only the key part is revealed and the remaining wrapping on the medical device is covering the rest of the device and particularly the controlling part 43 of the device. Therefore in handling the sterile single-use device of the embodiment of the invention the user knows only to contact the remaining wrap packaging and never to allow anything to contact the non-wrapped part of the device. Thereby by the indication of the wrapping an improvement in use is achieved.

Another form of indication occurs when a medical device can be used in various ways in different medical procedures. The single use medical device such as a scalpel 81 can have three different frangible operating lines 26, 27, 28.

This use can be emphasized by the first end portion 21 extending to the different frangible operating lines 26, 27, 28 being colour coded or otherwise indicatively distinguished. This could mean that a medical procedure that is only on the skin is coded purple and the first end portion 21 up to the first frangible operating line 26 is coloured purple and the user knows to remove the purple first end portion 21 revealing the required shallow key part forming the operative part 41 up to the line of the first frangible operating line 26. When further medical procedures require different key parts these are identified by different colours to allow the appropriate first end portion 21 up to the appropriate frangible operating line to be removed and reveal the appropriate key part of the sterile single-use device for use in a clean and sterile manner provided by the embodiment of the invention.

Operable

The article being operable with the key part able to come into direct contact with the patient while the packaging is still partially over the non-key part of the device. Operability for non-movable single use medical devices is able to be achieved with a fixed packaging having one or more frangible operating lines Transformable As the single use medical device can have moving parts the packaging needs to be able to freely move so as to not restrict the users control of the medical device.

The use of shrink wrap is not generally acceptable as there is always a resilient restricting force on the medical device providing by the heat shrink wrapping. This force on the medical device to restrict is in itself a contrary package to the intended use and stops the user having full control of the device. Instead operation has to be in opposition to or in compensation of the shrink wrapping, otherwise the shrink wrapping is needed to be fully removed.

It is therefore important that the packaging does not provide hindrances to its use and control by the user of controlling part to effect operation of the operating part.

The medical packaging that provides the intended control for movable devices has a body which is transformable to allow alteration of the footprint of the single-use medical device to enable operative use of the single-use medical device while the controlling part remains at least substantially within the second portion of the body. Preferably the transformability of the body is to allow non-resilient alteration of the footprint of the single-use medical device.

In another form the medical packaging can be transformable to alter the volume of the body holding the single-use medical device to enable operative use of the single-use medical device while the controlling part remains at least substantially within the second portion of the body.

Preferably the transformability of the body is to allow non-resilient alteration of the volume of the body holding the single-use medical device At least one part of the at least one first end portion transforms in a corresponding manner to the change of shape of an operative part of the single-use medical device.

At least one part of the at least one second portion transforms in a corresponding manner to the change of shape of a controlling part of the single-use medical device.

The medical packaging can have the at least one second portion, which is sized and shaped for substantially covering a controlling part of the single-use medical device, is changeable or relatively moveable to allow controllable usage of the operative part by the controlling part, while retaining coverage over substantially all of the controlling part of the single-use medical device.

The transformable change can be a changeable form of the packaging by one or more of being:
Flexible
Deformable
Expandible
Malleable
Compressible The transformability of the packaging can be achieved in various ways. These include:
a) The shaping and flexibility of the packaging such that parts can readily move relative to each other.
b) The use of gusseting between separate fingers covering separate relatively movable elements of the medical device
c) The use of pivoting welds between separate fingers covering separate relatively movable elements of the medical device
d) The use of expandable or contractable continuous telescopic wrapping able to provide change of volume or footprint.
e) The use of different density plastics so as to provide different flexibility of different connected panels Examples There are a number of different types of medical devices that can make use of one or more of the concepts in combination.

Referring to FIG. 2 there is shown an example of medical packaging 12 in which a single-use medical device for a scalpel 81 which is sealed in a shaped package having a first end portion 21 and a second portion 23 that together closely follow and enclose the shape of the scalpel but does not hinder use.

The scalpel 81 has an operative part 41 at one end, used for incisions, and a controlling part 43 at the other end, for holding and operating the operative part. The operative part is the key part of a medical procedure that is allowed to directly touch the patient.

The scalpel 81 in this example can be for the medical procedure of making an incision. Therefore the packaging includes a plurality of marked frangible operating lines 26, 27 and 28 on the body of the packaging 12 indicating the respective use that is not to be touched by the user and defining the particular key part forming the operative part 41 allowable to be in direct contact with the patient for the respective predefined use of:
a) Surface skin incision
b) Shallow incision
c) Deep incision.

Dependent on the medical event and therefore the medical procedure to be undertaken the user can select which depth of incision is to be required and thereby identify the required key part by the selection of the corresponding marked frangible operating lines 26, 27 and 28 on the body of the packaging.

The medical packaging 12 has a frangible connection 25 at each of the corresponding marked frangible operating lines 26, 27 and 28 on the body of the packaging. Selection of the required marked frangible operating lines 26, 27 and 28 and rupturing the frangible connection at that selected line will remove the relevant sized first end portion 21 to reveal the relevant key part forming the operative part 41 of the device.

Clearly the frangible connection 25 between the two parts 21, 23 is closer to the operative part 41, which is generally smaller than the controlling part 43, and is the only part contacting the patient. By activating the frangible connection 25 and removing a small first end portion 21 of the packaging 12, the operative part 41 of the enclosed device 81 can be exposed for its operative function without any direct touching of the device. Further the controlling part 43 of the device is held and used through the second portion 23 formed by the remainder of the packaging 12 and which remains around the device at all times, without any direct touching of the device by the user.

For further avoidance of hindrance of operation of the scalpel 81 the packaging 12 is loose fitting but allows a touch sensitive control through the second part 23 to the controlling part 43. As a forefinger of a user is on the top edge of the scalpel 81 when it is held in a pencil grip or in a pointing grip, there is the removal of seams or other joins at the critical touch points. This can for example mean a seam could be along the longitudinal symmetrical middle of the scalpel and not along top edges.

Referring to FIG. 3 this packaging 13 holds a sterile single-use medical device in the form of a double ended cotton bud 82. The packaging 13 has two first end portions 21 covering one each of two operative parts 41 at each opposing end of the single-use medical device and an intermediate central second portion 23 therebetween covering the central controlling part 43 of the double ended cotton bud 82.

The packaging 13 provides a choice of two corresponding marked frangible operating lines 26, 27 which can correspond to different medical procedures if they are sized differently or coated differently to be used as an applicator or merely to be used in sequence. There is further marked frangible operating line 28 for when the double ended cotton bud 82 is to be used as an insertion swab, for insertion in the mouth or ear or nose to obtain material sample.

The one of the two first end portions 21 to be detached at the respective frangible connection 25 from the central section portion 23 thereby selectively reveals one end of the single-use medical device that has two selective operative parts 41. Alternatively, each end can be removed so as to reveal the two operative parts of the single-use medical device such as double ended cotton buds so that the device is held in the central portion with the surrounding packaging 23.

In this form activating the frangible connection 25 and removing a small first end portion 21 of the package at each end simultaneously or sequentially provides the operative parts of the enclosed device to be exposed for its operative function without any direct touching of the device. Further the controlling part of the device is held and used through the remainder controlling part portion 23 of the packaging which remains around the device at all times, without any direct touching of the device by the user.

In each version, each frangible connection until used, provides protection for the enclosed single-use medical device, equal to the remainder of the package; produces an opening of predetermined size and shape, and is not subject to tearing beyond the predetermined limits; and is sufficiently anchored to resist accidental, premature tearing during handling of the package.

When embodiments of the invention are used, as the enclosed single-use medical device is not directly touched by the user at any time, the invention provides the benefit of an easier and more effective way to achieve the aseptic non-touch technique principles, minimizing contamination of the device by microorganisms in everyday procedures via contact, droplet and airborne transmission. By using embodiments of the invention, the aseptic non-touch technique principles can be upheld with reduced need for assistant staff, reduced risk of human error, reduced overall equipment resource burden and reduced waste burden when compared to existing methods.

Using embodiments of the invention enables the aseptic non-touch technique principles to be achievable by individuals who are not trained or experienced. The invention allows aseptic non-touch technique principles to be upheld irrespective of the environment, raising the level of cleanliness achievable in locations external to hospital such as homecare settings.

The invention substantially changes the use of the sterile sealed single-use medical device package, as the package is no longer removed and discarded, but rather, remains around the enclosed single-use medical device at all times, acting as a physical barrier, preventing the contamination of the device by microorganisms from contact, droplet and airborne transmission.

The invention provides embodiments of shaped movable packaging 14, 15 such as in FIGS. 4 and 5 for holding a movable shaped single-use medical device such as tweezers 83 or suture scissors 84. In these embodiments the packaging 14, 15 allows for holding in a sterile condition and usage of the single-use medical devices 83, 84 that require operative parts 41 to move relative to each other to form an operative end or require controlling parts to move relative to each other to form a controlling end or a combination thereof. The shaped movable packaging 14, 15 can hold such single-use medical device 83, 84 and allow them to be operatively moved while still substantially in the packaging.

Referring to FIG. 4 there is a packaging 14 that holds a sterile single-use medical device of tweezers 83. The packaging has an enclosing body of two first end portions 21 forming an enclosing sealed volume when connected with a bifurcated connected second end portion 23 formed at the opposing end and able to hold the single-use medical device 84 therein in a sterile condition.

The tweezers 83 in this example can be for the medical procedure of removing sutures but be usable in three ways. Therefore the packaging 14 includes a plurality of marked frangible operating lines 26, 27 and 28 on the body of the packaging indicating the respective use and the particular key part that is not to be touched by the user but needed to be in direct contact with the patient for the respective predefined use of:

a) Surface Skin Suture removal
b) Shallow Suture removal
c) Deep Suture removal.

The operation of the tweezers 83 while retained in the bifurcated second part 23 is that the two arms of the tweezers are allowed to bend towards each other by the movement means 62 of allowance by the form of the packaging of unhindered flexible movement.

Dependent on the medical event and therefore the medical procedure to be undertaken the user can select which depth of incision is to be required and thereby identify the required key part by the selection of the corresponding marked frangible operating lines 26, 27 and 28 on the body of the packaging 14.

The medical packaging 14 has a frangible connection 25 at each of the corresponding marked frangible operating lines 26, 27 and 28 on the body of the packaging 14. Selection of the required marked frangible operating lines 26, 27 and 28 and rupturing the frangible connection at that selected line will remove the relevant sized first end portion 21 to reveal the relevant key part forming the operative part 41 of the device.

Referring to FIG. 5 there is a medical packaging 15 that holds a sterile single-use medical device of suture scissors 84. The packaging 15 has an enclosing body of single first end portion 21 attached to a bifurcated second part 23 forming an enclosing volume and able to hold the single-use medical device therein in a sterile condition.

The first end portion 21 in this case is sized and shaped for substantially enclosing both blades of the suture scissors 84 and covering the two operative ends 41 in one first end portion 21. The plurality of operative parts 41 of the single-use medical device of the suture scissors 84 are pivotally connected at a central pivot 44 to allow control of the pivoted two operative parts 41 by corresponding action of the pivoted two controlling arms 43 with each controlling part 43 having respective finger section 47.

The shaping and structure of the connecting bifurcated second portion, the controlling parts 43 and the shaping, construction and material allows jointed pivotal movement 64 for the packaging 15 to be movable to allow the plurality of operative parts 43, by the user's fingers in the finger sections 47, to be pivotally moved around pivot 44 towards each other and due to the operative connection to the two operative parts 41 operatively effect function of the suture scissors 84 while the controlling part 43 including finger sections 47 remains in the second end portion 23.

There is an openable element 25 between the first end portion 21 and the bifurcated second portion 23 wherein the openable element 25 is able to be displaced into an open state at the time of use to allow removal of the first end portion 21 and reveal the key part forming the operative parts 41 of the single-use medical device 84 to be used while the second end 43 remains substantially within the second end portion 23.

The medical packaging 15 for covering a suture scissors 84 and the openable connection of packaging includes a plurality of marked frangible operating lines 26, 27 and 28 on the body of the packaging indicating the respective use and defining the particular key part that is not to be touched by the user but intended to be in direct contact with the patient for the respective predefined use of:
a) Surface Skin Suture removal
b) Shallow Suture removal
c) Deep Suture removal.

Dependent on the medical event and therefore the medical procedure to be undertaken the user can select which depth of suture removal is to be required and thereby identify the required key part by the selection of the corresponding marked frangible operating lines 26, 27 and 28 on the body of the packaging.

The medical packaging 15 has a frangible connection 25 at each of the corresponding marked frangible operating lines 26, 27 and 28 on the body of the packaging. Selection of the required marked frangible operating lines 26, 27 and 28 and rupturing the frangible connection at that selected line will remove the relevant sized first end portion 21 to reveal the relevant key part forming the operative part 41 of the device.

The medical packagings 14 to 19 of FIGS. 4 to 9 are transformable shaped packaging for holding a transformable shaped single-use medical device 83 to 87 that can be operatively moved while still substantially in the transformed packaging.

It can be seen that the medical packaging of FIGS. 4 and 5, allows transformation of the packaging due to the material 62 or pivotal jointed movement 64 allowed by the bifurcated second portion 23 covering the controlling parts 43 being shaped and the material and construction allowing movement without hindering the user's control of the device with the controlling parts 43. The structures of FIGS. 6 to 9 provide other transformation means 63, 65, 66, so as to allow alteration of the footprint of the single-use medical devices 84 to 87 to enable operative use of the single-use medical device while the controlling part 43 remains at least substantially within the second portion 23 of the body of the packaging 16 to 19. The transformability of the body is to allow unhindered alteration of the footprint of the single-use medical device. The transformability can be to alter the volume of the body holding the single-use medical device to enable operative use of the single-use medical device while the controlling part remains at least substantially within the second portion of the body.

Figure 6:
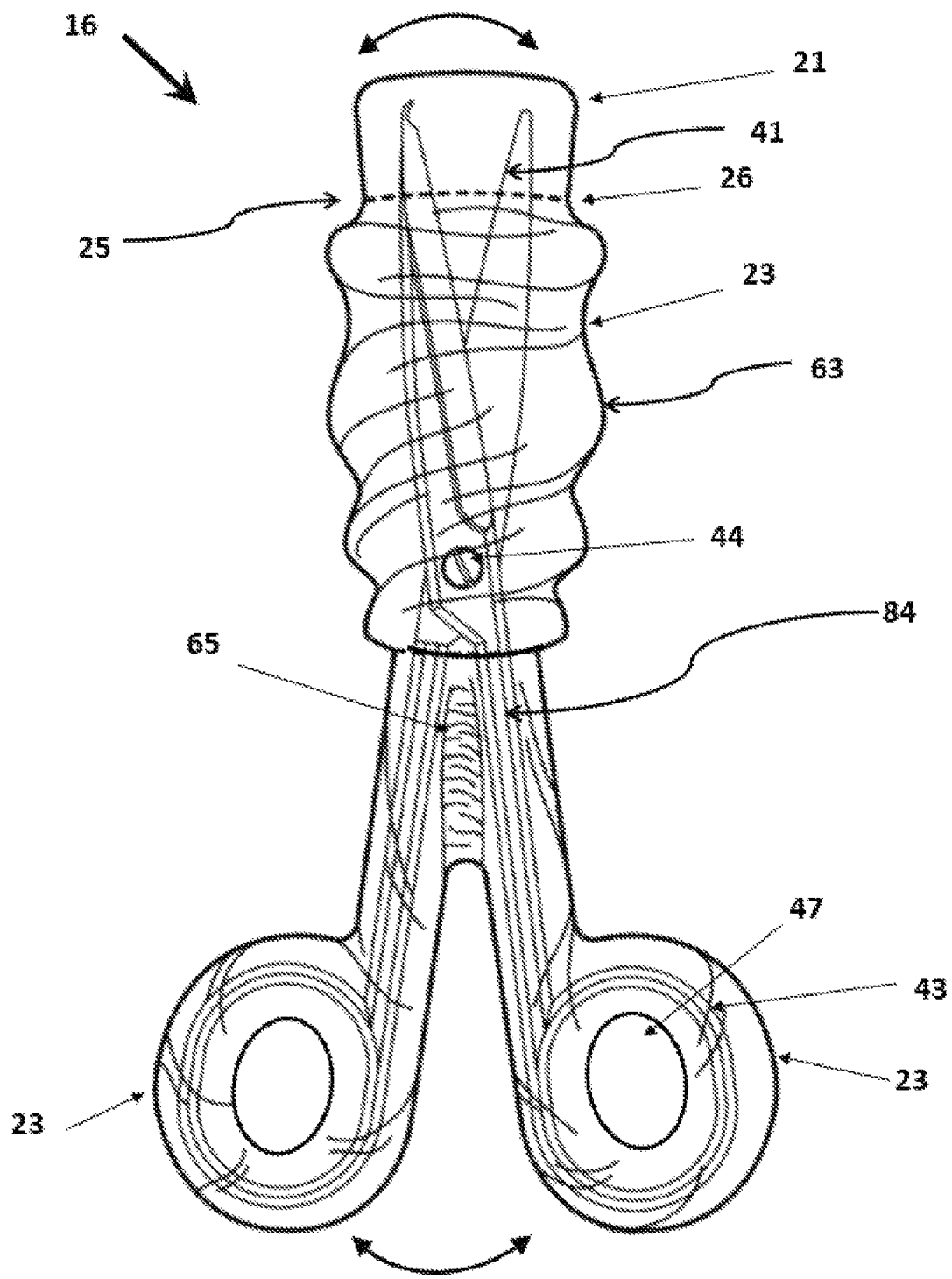
FIG. 6 is a diagrammatic view of a medical packaging that holds a sterile single-use medical device for holding the scissors of FIG. 5 in a different manner by a different transformable shaped package in accordance with another preferred embodiment of the present invention.

Referring to FIG. 6 there is a different medical packaging 16 to the medical packaging 15 of FIG. 5 for holding the same sterile single-use medical device of suture scissors 84. The packaging 16 has an enclosing body forming an enclosing volume with a single first end portion 21 and a bifurcated second end portion 23 able to hold the single-use medical device therein in a sterile condition.

This medical packaging 16 has the second portion 23 including a lateral expansion section 63 that covers the parts of the arms of the scissors 84 that do not form part of the key part and therefore are not the key part forming the operative part 41 of the scissors but need to be covered by the second portion 23. These parts of the arms are on the same side of the pivot 44 as the operating part 41 and on the distal side to the controlling part 43 and finger control holes 47.

The lateral expansion section 63 of the second portion 23 of the medical packaging 15 allows free unhindered lateral movement of the parts of the arms of the scissors 84 that do not form part of the key part. Therefore only the operative part 41 of the scissors 84 are revealed but use is unhindered.

As the controlling part 43 of the scissors on the distal side of the pivot also need to pivotally move around the pivot 44 but remain within the remaining closed part of the second part 23 there is include a sealed gusset 65 that allows such movement unhindered. This gusset extends between the controlling part 43 of the scissors having the pivoting handles with finger control holes 47. The gusset allows unhindered use of the pivotal controlling parts 43 while remaining in a sealed sterile environment.

There is an openable element 25 between the first end portion 21 and the second portion 23 wherein the openable element 25 is able to be displaced into an open state at the time of use to allow removal of the first end portion 21 and reveal the key part forming the operative parts 41 of the single-use medical device 84 to be used while the second end 43 remains substantially within the second end portion 23.

The medical packaging 16 for covering a suture scissors 84 and the openable connection of packaging includes a single frangible operating line 26, on the body of the packaging indicating the respective use and defining the particular key part that is not to be touched by the user but intended to be in direct contact with the patient for the respective predefined use.

As can be seen, the medical packaging can include different combinations of unhindered movement means such as movement means 62 to 66. Further other forms of pivoting sterile single-use medical devices such as standard scissors, surgical scissors, ring forceps etc can make use of the novel medical packaging.

In these embodiments the first end portion 21 is an outer body enclosure covering the plurality of operative ends 41 that move relative to each other so as to be functional. Due to the length of the operating part to a central pivot 44, a single first end portion 21 is usually used rather than a plurality of first end portions such as used for the packaging of the tweezers 83 of FIG. 4. The controlling part 43, or a plurality of controlling parts 43 are moved relative to each other around the central pivot 44 to create the functional operation. The packaging includes a plurality of second portions 23 that by the selection of movement means 62 to 66 can move relative to each other and allow unhindered use of the controlling parts 43 while remaining in the second portions 23.

The single first end portion 21 extends to one opening frangible line 26 below the central pivot 44 of the scissors. The plurality of second end portions 23 in this case are sized and shaped for substantially following the shape and covering a controlling part 43 being the finger grips 47 of the single-use medical device 84. Therefore, the second portions 23 are formed of shaped bifurcated finger holding sections covering each extension of the finger holding portions 47 of the scissors.

The shaping of the bifurcated finger sections of the second portions 23 and the joined first end portion 21 and the structure, location and integration of unhindered movement means such as movement means 62 to 66 into the second portion 43 of the packaging allows for the controlling parts 43 to be movable to allow the finger sections 47 to be moved towards each other and effect a similar action of the two pivoting operative parts 41 on the other side of the pivot 44 while the controlling part 43 remains in the second portions 23.

There is an openable element 25 on at least part of the first end portion 21 wherein the openable element on at least part of the first end portion is able to be displaced into an open state at time of use to allow operative part 43 of the single-use medical device to be used while the second end 43 remains substantially within the second end portion 23.

Figure 7:
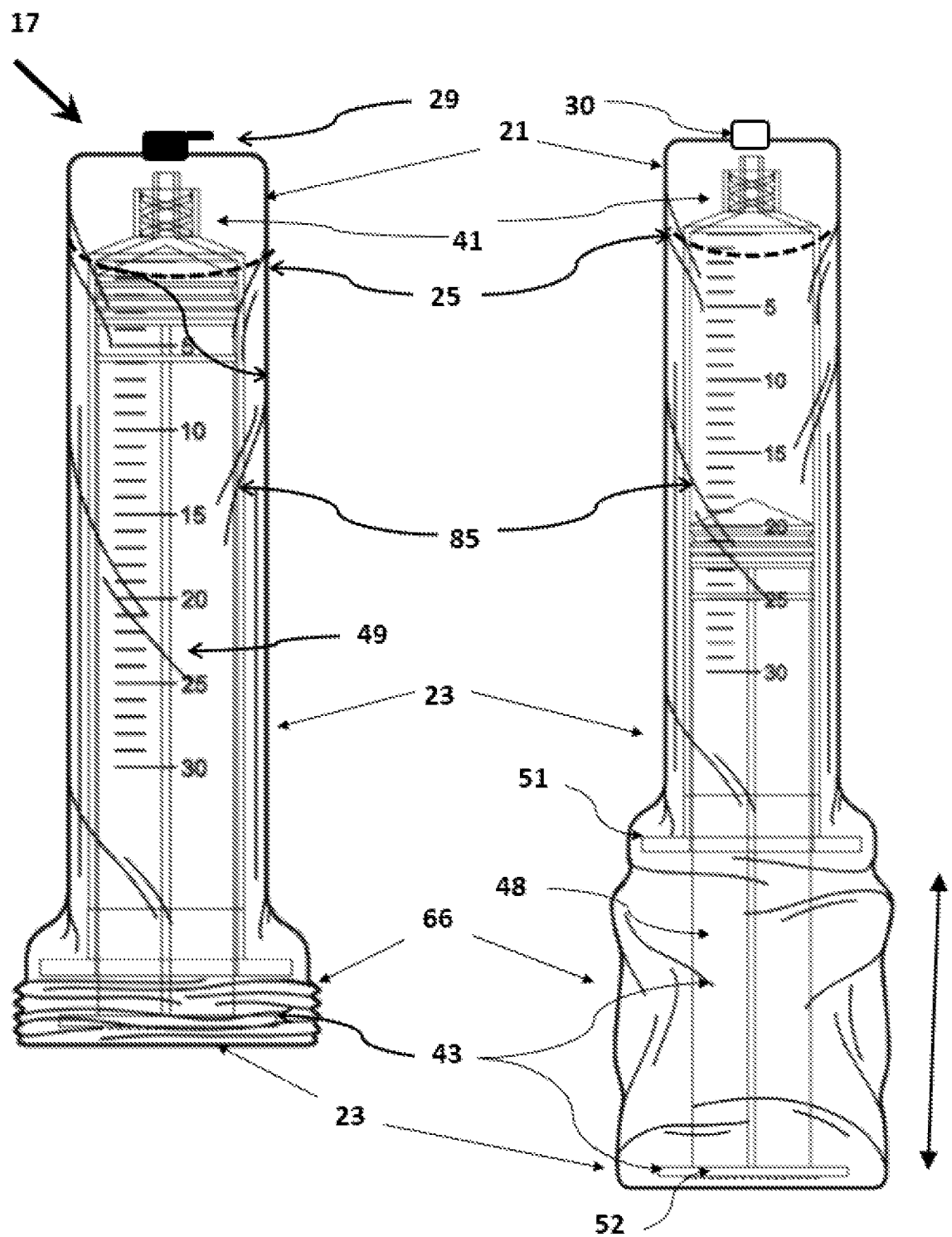
FIG. 7 are two diagrammatic views of a medical packaging that holds a sterile single-use medical device in the form of a syringe in first transportable state and second extended operable state in accordance with another preferred embodiment of the present invention having the medical packaging being transformable by allowing unhindered extending action initiated by user with finger control of the plunger while still in the second portion of the packaging.

Referring to FIG. 7 there is shown a medical packaging 17 that holds a sterile single-use medical device in the form of a syringe 85 for dispensing of the contents of the syringe upon plunging the controlling part 43 of the plunger 48 into the central cylindrical body 49 and expelling through the operative part 41.

The controlling part 43 including the barrel flange 51 at the open bottom of the central cylindrical body 49 and the plunger flange 52 at the bottom of the plunger 48 so that operation by the user is by two fingers extending around the central cylindrical body 49 and against the barrel flange 51 and thumb depressing plunger flange 52 to insert the plunger 48 into the central cylindrical body 49. Similarly in reverse, partial extraction of the plunger is required to effect drawing in of required sterile material whether saline for cleaning, medicine or other treatment material. This partial extraction is effected by holding the central cylindrical body 49 and pulling on the plunger flange 52 of the plunger away from the barrel flange 51 until required quantity is shown by the graduated scale on the outside of the central cylindrical body 49.

The medical packaging 17 for the syringe 85 is required to allow this operation in an unhindered manner while proving a sterile and clean usage. The medical packaging of FIG. 7 has two parts, being a first end portion 21, connecting to a second portion 23 that covers and encloses the syringe 85 in a sealed sterile condition. There is a frangible connection 25 between the first end portion 21 and the second portion 23.

The second portion 23 has a first part that covers the central cylindrical body 49 and is transparent to allow viewing of the graduated scale on the outside of the central cylindrical body 49 or includes a window to allow viewing. The second portion 23 has a second part that covers the plunger 48 as it protrudes from the central cylindrical body 49. As the footprint and volume of the medical device 85 changes the footprint and volume of the packaging 17 needs to be able to change. The second part that covers the plunger 48 is a telescopic transforming means 66 that can be a sealed expanding concertina section to allow ready extension in a longitudinal manner to the maximum extent of the plunger 48 from the central cylindrical body 49.

The first end portion 21 includes a preparation frangible openable connection 29 which can be moved from a closed state to an open state to allow a sterile needle to be attached that acts as the conduit from a sterile vial containing the required material.

In use by activating the frangible connection 29 and opening the smaller opening 30 of first end portion 21 of the package 17 to form the preparation frangible openable connection and can be exposed for its operative function, without any direct touching of the device. Further the controlling part 43 of the device can be held around the second portion 23 covering the central cylindrical body 49 and the plunger 48 can be extracted while within the transformable telescopic part 66 while remaining sealed in the second portion 23 and thereby controlled unhindered through the remainder of the packaging 17. The second portion 23, and the transformable part being the telescopic transforming means 66, so that the second end portion 22 remains around the device at all times, without any direct touching of the device by the user.

The invention allows for the small end opening 29 in the first end portion 21 for a sterile needle, in its sterile packaging, to be attached to the single-use sterile syringe while still enclosed in the package. As the attaching part of the needle is sterile, the sterility of the syringe is maintained. Once attached, the small end opening 30 can be closed around the needle, protecting the sterility of the enclosed syringe. This allows medicine or other contents to be drawn into the barrel while the syringe remains totally within the packaging in its sterile environment. As the syringe remains completely covered by the sterile package, it can be placed on a non-sterile surface for transport to the patient's location without compromising its sterility. When ready for administration, the second openable element on the first end portion 21 of the package is able to be displaced into an open state to allow the operative part of the syringe to be used in contact with the patient or the patient's intravenous port.

It can be seen therefore that the single-use medical device of the syringe 85 is a transformable shaped body as the plunger fits within the central cylindrical body 49 and therefore changes its length and shape. The packaging 17 is formed by an enclosing material that has a body forming an enclosing volume with a first end portion 21 and a second end portion 23 with a transformable intermediate part 66 so as to be able to hold the single-use medical device therein in a sterile condition whether that device is in an extended or contracted form.

The packaging can have at least one openable element 21 at an end allowing the syringe after being filled and placed in a ready to use condition and the first end portion 21 displaced into an open state at time of use to allow operative part 41 to be revealed and the single-use medical device to be used by use of the controlling part 43 while remaining within the second end portion 23. However, the expandable concertina portion 66 that allows for retaining a sterile outer protection over a range of lengths of the single-use medical device in the form of a syringe 85.

Figure 8:
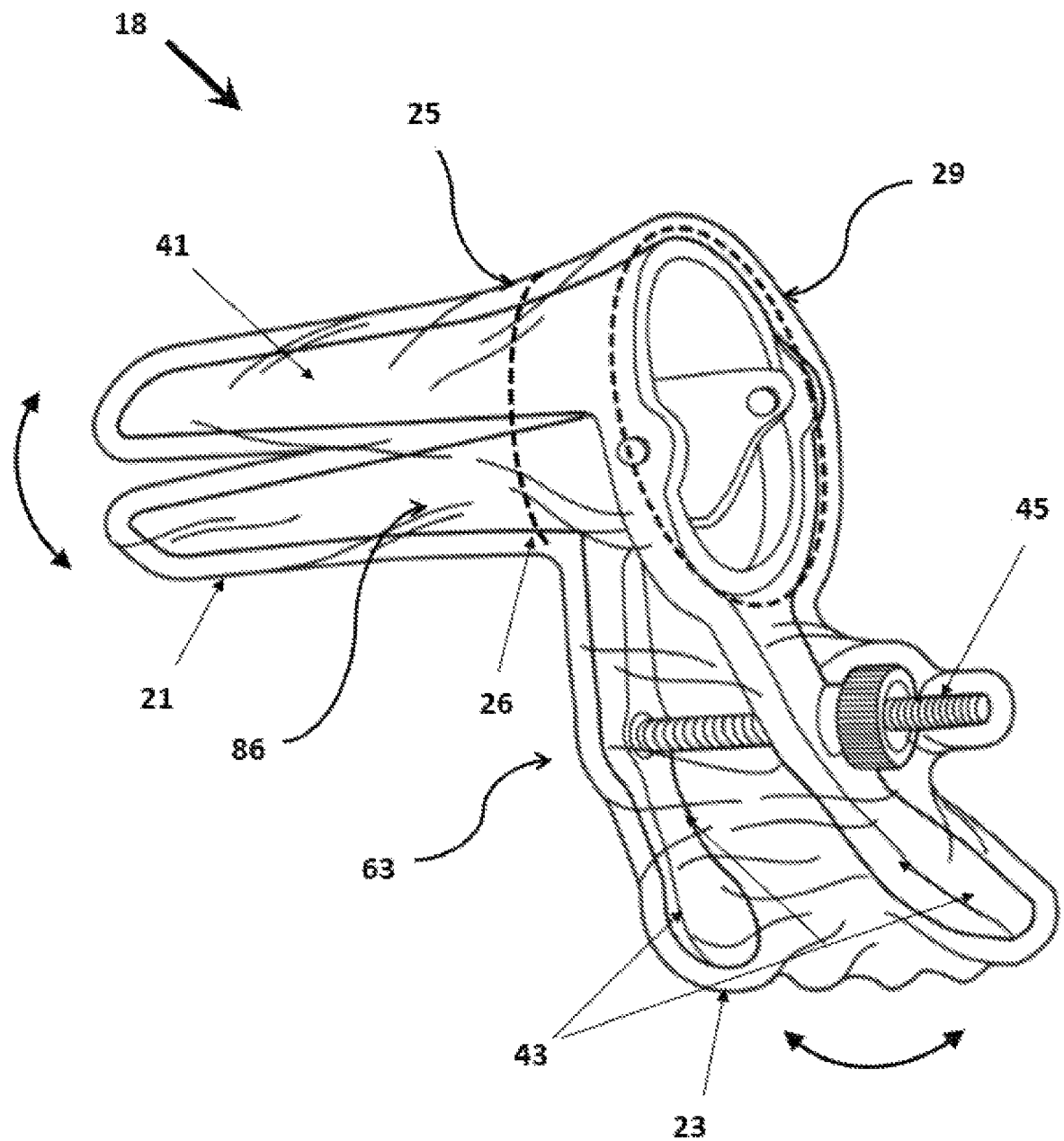
FIG. 8 is a diagrammatic view of a medical packaging that holds a sterile single-use medical device in the form of a vaginal speculum in accordance with another preferred embodiment of the present invention having an openable connections so that a selected first end portion can be removed to show the relevant key part for the relevant selected medical procedure and a secondary frangible connection able to be opened for insertion of other instruments therethrough and with the medical packaging being transformable by allowing pivoting action initiated by user with finger control of the screw threaded expander while still in the second portion of the packaging.

Referring to FIG. 8 there is a medical packaging 18 that holds a sterile single-use medical device in the form of a vaginal speculum 86. The medical packaging includes a first end portion 21 and a second end portion 23 for enclosing the sterile single-use medical device.

The first end portion of the medical packaging 18 covers an adjustable opening duck-bill structure. The medical packaging 18 has an openable connections 25 so that a selected first end portion 21 can be removed to show the relevant key part forming the operative part 41 for the relevant selected medical procedure and a secondary frangible connection 29 able to be opened for insertion of other instruments therethrough.

The medical packaging is transformable by allowing pivoting action initiated by user with finger control of the screw threaded expander while still in the second portion of the packaging. The medical packaging 18 includes the second portion including a part being a lateral expansion movement means 63 allowing change of footprint or volume to allow expansion and unhindered control of the controlling parts 43 of the clamp handles and the screw thread adjuster 45 while remaining covered by the second portion 23.

Figure 9:
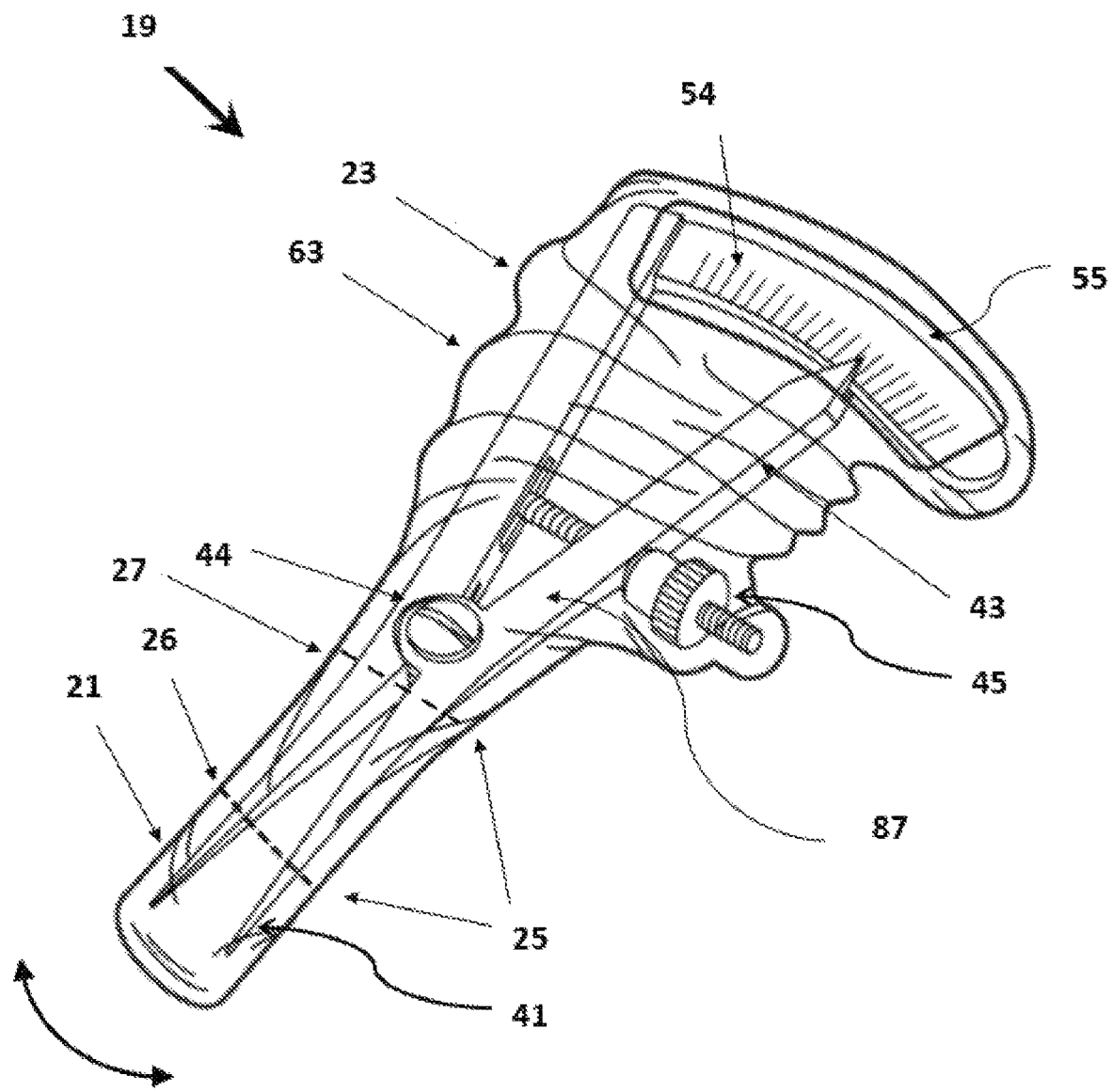
FIG. 9 is a diagrammatic view of a medical packaging that holds a sterile single-use medical device in the form of a set of caliper and ruler in accordance with another preferred embodiment of the present invention having a frangible operating lines identifying the key part of the device and having openable connections at that line so that a selected first end portion can be removed to show the relevant key part for the relevant selected medical procedure and the medical packaging being transformable by allowing pivoting action initiated by user with finger control of the screw threaded expander while still in the second portion of the packaging with the rule part viewable through a clear window.

Referring to FIG. 9 there is a medical packaging 19 that holds a sterile single-use medical device in the form of a set of caliper and ruler 87. The medical packaging includes a first end portion 21 and a second end portion 23 for enclosing the sterile single-use medical device.

There are frangible operating lines 26 and 27 identifying the key part of the device according to different uses and the category of range of expansion of the caliper arms forming the operating part 41 required around the pivot 44. The packaging has openable connections 25 at each line so that a selected first end portion can be removed to show the relevant key part for the relevant selected medical procedure and the medical packaging being transformable by allowing pivoting action initiated by user with finger control of the screw threaded expander 45 while still in the second portion of the packaging.

The medical packaging is transformable by allowing pivoting action initiated by user with finger control of the screw threaded expander 45 while still in the second portion 23 of the packaging 19. The medical packaging 19 includes the second portion including a part being a lateral expansion movement means 63 allowing change of footprint or volume to allow expansion and unhindered control of the controlling parts 43 including the screw thread adjuster 45 while remaining covered by the second portion 23. The rule 54 on the caliper and rule which measures the pivoting action initiated by user with finger control of the screw threaded expander 45 can be viewable through a window 55 of the second portion 23 while the device is still in the second portion of the packaging such that use and control of the device is unhindered with the rule part viewable through the clear window.

Figure 10:
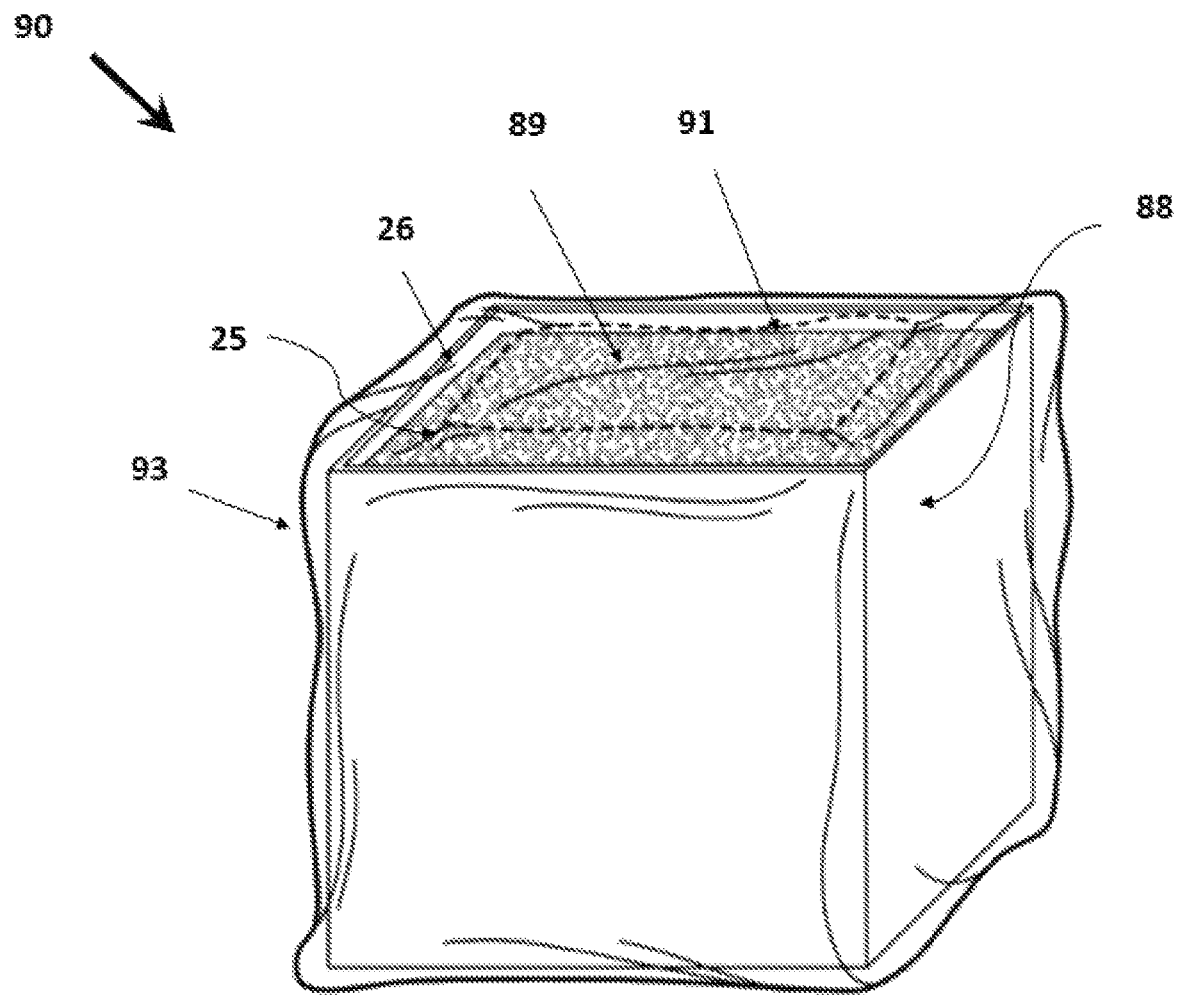
FIG. 10 is a diagrammatic view of a medical packaging that holds a sterile single-use medical device in the form of a sterile rest box in accordance with another preferred embodiment of the present invention having a frangible operating line identifying the key part of the device and having openable connections at that line so that a selected first end portion can be removed.

Referring to FIG. 10 there is a medical packaging 90 that holds a sterile single-use medical device in the form of a sterile rest box 88. The medical packaging 90 includes a first end portion 91 and a second end portion 93 for enclosing the sterile single-use medical device such as sterile foam 89 or other sterile receiving material or structures to only receive key parts of other single use medical devices while in the middle of a medical procedure and requiring a different device to be used before returning to this device.

The medical packaging 90 includes a frangible operating line 26 identifying the key part of the device and having openable connections 25 at that line so that a selected first end portion 91 can be removed from the second portion 93 revealing only the key part 89. By only the sterile non contaminated key part of the other sterile single-use medical device coming in contact with the sterile non contacted key part of the clean and sterile condition of the medical procedure is maintained.

Other Combinations

The medical packaging can be for single ended operative parts or multiple ended operative parts. There can be one end of the device with an operative end. The operative end could be fixed with single operative part or be movable and work due to relative motion of plurality of operative parts.

However the single-use medical device can include a plurality of operative parts 41 at each end of a central controlling part 43. This requires a packaging with a plurality of first end portions 21 connected to a second portion that extends and connects therebetween and forms a second central portion 23. Such packaging allows for selective use of one or more ends of a single-use medical device. This can be so that one end can be used selectively after the other end such as in the case of a cotton bud, or it could be so that the single-use medical device has different sizes or different uses so that the user can select the appropriate end and use that end. An example can be a tongue depressor that has one end sized for a larger person or adult while the other end is sized for a smaller person or child.

It can be seen that the invention includes various forms of fixed, shaped, movable and transformable packaging parts together with a thickness flexibility and transparency of the packaging such that the single-use medical device can be used and fully controlled by the user by holding the controllable part 43 of the device while still substantially within the second portion 23.

This can be in the form of a concertina gusset between finger joints of the packaging so as to provide a transformation of shape of the packaging and relative movement of either or both of the operative and controlling parts of the single-use medical device while remaining substantially within the second end portion which is held by the user.

Figure 11:
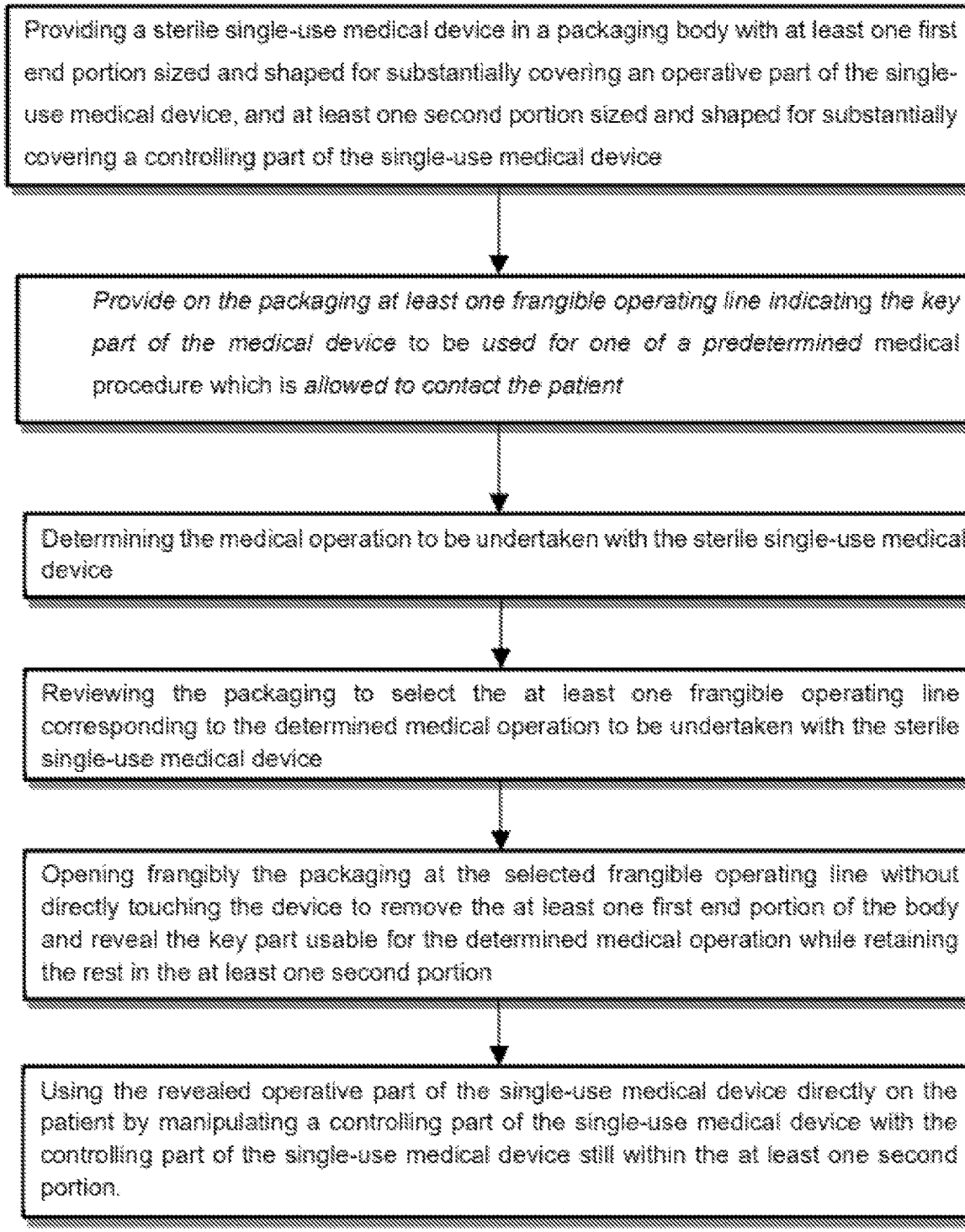
FIG. 11 is a diagrammatic view of an illustrative embodiment of a method of providing a usable sterile single-use medical device in a continuing clean or sterile manner in accordance with an embodiment of the invention.

Referring to FIG. 11 there is shown that embodiments of the invention also provide a method of providing a usable sterile single-use medical device in a continuing sterile manner including the steps of:

a) Providing a sterile single-use medical device in a flexible packaging body forming an enclosing volume with at least one first end portion and at least one second portion able to hold the single-use medical device therein in a sterile condition wherein the at least one first end portion sized and shaped for substantially covering an operative part of the single-use medical device, and the at least one second portion sized and shaped for substantially covering a controlling part of the single-use medical device b) Providing at least one openable element on at least part of each of the at least one first end portion of the body c) Holding the at least one second portion with the controlling part of the single-use medical device still within the at least one second portion d) Opening the at least one openable element of the at least one first end portion of the packaging by removing breaking or opening at least part of the at least one first end portion to reveal the at least one operative part of the single-use medical device without directly touching the device and e) Using the revealed operative part of the single-use medical device by manipulating a controlling part of the single-use medical device with the controlling part of the single-use medical device still within the at least one second portion.

In a particular form the method comprises the user undertaking the steps of a) Providing a sterile single-use medical device in a packaging body with at least one first end portion sized and shaped for substantially covering an operative part of the single-use medical device, and at least one second portion sized and shaped for substantially covering a controlling part of the single-use medical device b) Providing on the packaging at least one frangible operating line indication the key part of the medical device when used for one of a predetermined medical procedure to be undertaken with the sterile single-use medical device key part of Providing at least one frangible operating line indicating the key part of the single-use medical device allowed to contact the patient c) Determining the medical procedure to be undertaken with the sterile single-use medical device d) Reviewing the packaging to select the at least one frangible operating line corresponding to the determined medical procedure to be undertaken with the sterile single-use medical device e) Opening frangibly the packaging at the selected frangible operating line without directly touching the device to remove the at least one first end portion of the body and reveal the key part usable for the determined medical procedure while retaining the rest in the at least one second portion f) Using the revealed operative part of the single-use medical device directly on the patient by manipulating a controlling part of the single-use medical device with the controlling part of the single-use medical device still within the at least one second portion.

The at least one part which corresponds in shape to an operative part of the single-use medical device.

The at least one part which transforms in a corresponding manner to change of shape of a controlling part of the single-use medical device It can be seen that the invention in various forms allows a single-use only sterile sealed package used to enclose a single-use medical device. An operative part of the enclosed device can be exposed for its function while the controlling part of the device is held and manipulated by the user through the remainder of the packaging which remains around the device at all times. Therefore, the device can be used without being directly touched by the user. This minimizes contamination of the device by microorganisms via contact, droplet and airborne transmission in a fast, simple, reliable and straight-forward manner.

Advantages of embodiments of the present invention include the following singly or in combination:

Physical Barrier to cross-contamination during use of device—embodiments of the present invention maximise the benefit of the sterile single-use medical packaging as the best asset for maintaining sterility of the enclosed device, by retaining the packaging as a protective barrier substantially covering the device throughout its use. The packaging serves as a physical barrier that fully protects the enclose device against all contact, droplet, and airborne spread of pathogenic microorganisms.

The first portion of the packaging covers the key part and is retained as a barrier throughout all preparation time, and only removed at the last moment before use of the enclosed device. This minimises the amount of time the key part is exposed, therefore minimising the possibility of contact, droplet and airborne cross-contamination of the key part.

The second portion of the packaging covers the controlling part and is retained as a barrier between the user and the device for the entire procedure. The device remains substantially enclosed within its packaging at all times, and the user never directly contacts the device while performing the procedure.

As a result, contact cross-contamination of the device is avoided. Droplet and airborne cross-contamination of the key part is minimized as the key part is only exposed at the last moment before use, leading to a cleaner or even sterile everyday procedure that can only be achieved with the present invention.

Facilitates adherence to standard aseptic non-touch technique principles—In everyday procedures, the present invention provides a simpler, faster and more effective means to uphold aseptic non-touch technique principles. The first aseptic non-touch technique principle is to always decontaminate hands effectively. When decontaminating hands is not possible or not performed, for example in areas of water scarcity, the present invention provides an effective alternative to the need to perform hand-hygiene, allowing the device to be used by the healthcare worker without any direct touching of the device. As the device is never directly touched by the user, the cleanliness of the procedure is not reliant upon the ability of the user to perform hand-hygiene.

The second aseptic non-touch technique principle is to never contaminate the key part of a device or the key site of a patient. The present invention acts as a constant visual and physical indicator of the location of the key part of the device, substantially assisting the user to identify, be aware of and protect the key part. Droplet and airborne cross-contamination of the key part is minimized as the packaging covering the key part is retained until the last moment before of the device.

The third aseptic non-touch technique principle is to touch non-key parts with confidence. The non-key part of the device is the controlling part which remains enclosed in the second portion of the packaging throughout use of the device. Using the present invention, the enclosed device can be operated without any direct touching of the non-key parts of the device.

The fourth aseptic non-touch technique principle is to take appropriate infection prevention and control precautions. The present invention reduces reliance on hand-hygiene if it is not possible or not performed, reduces reliance on secondary resources and secondary equipment and reduces reliance on the presence of a clean environment and assistant staff.

Reduced reliance on secondary resources, equipment and assistant staff.—The present invention provides a means of achieving aseptic non-touch technique which is not reliant on secondary resources, equipment or assistant staff. The benefits of this are significant. The invention allows for use of an enclosed single-use medical device in a clean or sterile manner simply and time efficiently.

A greater degree of cleanliness can be achieved in healthcare environments external to the hospital, such as a medical clinic or external environments such as in the field. There is a significant reduction in waste from by everyday medical procedures. Secondary resources and equipment are freed up for competing uses in healthcare environments. There is less reliance on assistant staff to achieve a clean or sterile procedure, which is particularly emphasized in scenarios such as a lone first responder situation.

Patients in resource scarce countries can enjoy the benefit of a clean or sterile procedure where secondary resources, equipment or assistant staff are unavailable. The present invention can also reduce resource burden in developed countries. As an example, the COVID-19 pandemic lead to a depletion of hand sanitiser in major hospitals in many developed countries. A situation such as this would not have any negative impact on the ability of this invention to provide clean or sterile use of single-use medical devices.

Reduced risk of human error even without medical training and experience—The present invention simplifies the achievement of aseptic non-touch technique and assists the user with key part identification and protection. There is a reduced risk for human error as the success of aseptic non-touch technique with the invention is less reliant on variables such as user hand-hygiene competency, experience of the user, ability of the user to self-identify the key part, ability of the user to manage an aseptic field, ability of the user to remove or avoid environmental contaminants, availability of secondary equipment or resources and availability of assistant staff.

The present invention allows aseptic non-touch technique to be achievable even by persons without any medical training or experience.

Reduced wastage—Volume of waste is reduced as the present invention is sized and shaped for the enclosed sterile single-use medical device. Volume of waste is reduced as there is significantly less reliance on secondary equipment and resources.

Human resources consumption is reduced—there is significantly less reliance on assistant staff. Time spent on everyday medical procedures is reduced as the present invention allows for simpler adherence to aseptic non-touch technique principles.

Graduated exposure of key part—The user of the sterile single-use medical device can select the extent to which they wish to expose the key part of the device for the predetermined use. This ensures that only the amount of the key part which is required for the procedure is exposed, minimizing the potential for cross-contamination of the key part by droplet and airborne pathogenic microorganisms.

Facilitates aseptic non-touch technique in urgent or emergent situations—As the present invention is not reliant on hand hygiene or the ability of the user to remove environmental contaminants, in urgent, emergent or challenging situations, both inside and external to the hospital, the present invention allows for the achievement of aseptic non-touch technique in a simpler, more straight forward, and more efficient manner than what is currently possible.

Aseptic non-touch technique achievable in the field—Consider the example of a first responder on a beach using the present invention enclosing a syringe. The syringe can be used to draw up medications while the key part and non-key parts remain enclosed and protected from contamination within the packaging.

A sterile needle may be attached to the needle hub, through a small frangible connection at the tip of the syringe packaging. If the drawing up process is interrupted or prolonged, the syringe, still in its complete packaging, can be set down on any surface, and remain fully protected.

Secondary equipment such as trolleys and dishes are unnecessary—When ready for use, the first portion of the packaging is removed to expose the key part of the syringe for it use. The plunger and barrel remain within the packaging and protected at all times throughout the procedure. This ensures that the syringe contents can be dispensed without contamination with pathogenic microorganisms or physical debris via the plunger. If the first responder accidentally pulls the plunger too far back and exposes the rubber stopper, the syringe could still be used safely as the rubber stopper always remains within the sterile environment of the packaging. If the first responder is unable to decontaminate hands, the syringe can still be used according to aseptic non-touch technique principles, as it is never directly touched by the user.

Aseptic non-touch technique achievable in resource scarce countries—The present invention allows aseptic non-touch technique principles to be achieved in resource scarce countries. In countries suffering water scarcity, poor sanitation, contaminated water supplies or deficient water infrastructure, the present invention allows for achievement of aseptic non-touch technique without reliance on hand hygiene or secondary equipment and infrastructure. In countries with deficient training, poor compliance systems or medical staff shortages, the present invention acts as a physical and visual indicator to assist in identifying and protecting the key parts of the device, allowing aseptic non-touch technique to be achieved in a simpler manner with less reliance on training, experience, secondary equipment, secondary resources and assistant staff.

Physical and visual indicator to allow easy identification and protection of key parts—The packaging serves as a physical and visual indicator of the key parts and non-keys part of the sterile single-use medical device. The first end portion covers the key part of the device, and the second portion covers the non-key part of the device. Differentiating key parts from non-key parts is derived from evidence-based literature. This differentiation allows users regardless of training or experience, to readily identify, be aware of and protect the key parts of the single-use device. The invention allows the first portion to cover key part of the device until the last moment before use, meaning the key parts are completely protected during device preparation procedures.

Protection against droplet or airborne transmission of pathogenic microorganisms in everyday procedures. Presently, outside of an operating suite, single-use medical devices are exposed to droplet and airborne cross-contamination. The present invention allows a physical barrier to be retained around the sterile single-use medical device throughout its function, protecting it from droplet and airborne transmission of pathogenic microorganisms. Only the key part of the device is exposed, and this is covered and protected by the packaging until the last moment before its use.

The packaging can have a plurality of tear line seals so that the user only exposes the smallest portion of the key part necessary according to its predetermined use, ensuring the device is maximally protected from droplet and airborne cross contamination while remaining functional for its use.

Protection of syringe plunger—The present invention incorporates a telescopic segment, such as an expanding and contracting concertina portion, which covers the plunger at all times during its use. The packaging allows for hindrance-free, non-resilient movement of the plunger. Therefore, the plunger is protected against contact, droplet and airborne contamination by pathogenic microorganisms as well as liquid or solid debris.

The inside surfaces of the syringe barrel are protected as well as the syringe contents from cross-contamination. The present invention is also applicable to syringes connected to an external apparatus such as a syringe pump.

Hazardous drug contamination of syringe plunger—The present invention remains around the syringe plunger and barrel at all times. In the event the plunger became contaminated with a hazardous drug, the packaging acts as an impervious physical barrier, so the workplace and any medical or public personnel are protected from cross-contamination by the contaminated syringe.

Improved compliance and compliance monitoring of aseptic non-touch technique—Aseptic non-touch technique standardises the approach to general aseptic technique. The present invention further standardises aseptic non-touch technique, removing reliance on number of user and environmental related variables and simplifying the procedure, improving ease of compliance and facilitating ease of compliance monitoring.

Interpretation

Embodiments

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment but can. Furthermore, the particular features, structures or characteristics can be combined in any suitable manner, as would be apparent to one of ordinary skill in the art from this disclosure, in one or more embodiments.

Similarly, it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Different Instances of Objects

As used herein, unless otherwise specified the use of the ordinal adjectives "first", "second", "third", etc., to describe a common object, merely indicate that different instances of like objects are being referred to and are not intended to imply that the objects so described must be in a given sequence, either temporally, spatially, in ranking, or in any other manner.

Specific Details

In the description provided herein, numerous specific details are set forth. However, it is understood that embodiments of the invention can be practiced without these specific details. In other instances, well-known methods, structures and techniques have not been shown in detail in order not to obscure an understanding of this description.

Terminology

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

Meanings of Specific Terms Throughout this Document are:
  a) Sterile and clean—means above normal environmental conditions to medical asepsis conditions
  b) Medical device—means a device for use on human patients, animal patients or for use in other biological procedures requiring sterile and clean environment including research, development and manufacture.
  c) Single-use device or Sterile single-use device—means a device for usage with direct contact to a patient in a sterile and clean manner with disposal after a single use.
  d) Microorganisms—means primarily pathogenic microorganisms when related to obtaining sterile and clean conditions for medical treatment of humans. However, it is to understood to include microorganisms in general when obtaining sterile and clean in other environments
  e) Contamination—means making not sterile or clean from pollution by particulates or infection by bacteria and other microorganisms and particularly from pathogenic microorganisms and further includes cross-contamination where there is unintentional transfer from one substance or object to another, with harmful effect.
  f) key part—means the part of a device which comes into direct contact with the patient's skin, or an injection port and therefore must remain sterile
  g) operative part is the part of the device that forms the key part and must not be touched by the user but is able to be operatively engaged in direct contact with the patient in use.
  h) non-key part means the remaining part of a device which is not necessary to come into direct contact with the patient's skin, or an injection port and therefore must remain away from contact with the patient.
  i) controlling part is at least some of the non-key part of the device that is needed to be manipulated by the user in order to effect use of the operative part
  j) Transformable packaging means changing of footprint or volume of packaging or change of relative location of parts of the packaging to allow hindrance free operation of single use medical devices that have moving parts.

Comprising and Including

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and further modifications can be made thereto without departing from the spirit of the invention, and it is intended to claim all such changes and modifications as fall within the scope of the invention. For example, any formulas given above are merely representative of procedures that can be used. Functionality can be added or deleted from the block diagrams and operations can be interchanged among functional blocks. Steps can be added or deleted to methods described within the scope of the present invention.

Although the invention has been described with reference to specific examples, it will be appreciated by those skilled in the art that the invention can be embodied in many other forms.

INDUSTRIAL APPLICABILITY

It is apparent from the above, that the arrangements described are applicable to the medical packaging that holds a sterile single-use medical device industries and to the medical industries that use such devices.

The invention claimed is:

1. A medical packaging for holding a sterile single-use medical device, wherein the medical device has at least one operative part which in use is a key part for direct contact to a patient and further has at least one controlling part for controlling the at least one operative part, the packaging including: a body forming an enclosing volume able to hold a single-use medical device in a sterile condition, the body having at least one first end portion, at least one second end portion and at least one openable connection between the at least one first end portion and one or more of the at least one second end portion to allow the at least one first end portion to be disconnected from the at least one second end portion wherein:
   i. the at least one first end portion is sized and shaped for substantially covering one or more operative parts of the single-use medical device;
   ii. at least part of one or more of the at least one second end portion is sized and shaped for substantially covering one or more controlling parts of the single-use medical device;
   iii. the at least one openable connection is able to have the at least one first end portion displaced into an open state at time of use to allow the at least one operative part of the single-use medical device to be revealed and usable directly on the patient; and
   iv. the at least one second end portion remains substantially covering one or more controlling parts of the single-use medical device and allows the at least part of the at least one operative part to be controlled by the at least one controlling part while the at least one controlling part remains substantially within the at least one second end portion,
      wherein the second end portion is a plurality of jointed second end portions which include finger location holes to allow the user to use fingers on controlling parts of the single-use medical device while the at least one controlling parts of the single-use medical device remains in the second end portions.

2. A medical packaging according to claim 1 wherein the body is substantially flexible to allow the user to hold and operate the enclosed sterile single-use medical device without touching the device still substantially enclosed in the packaging body.

3. A medical packaging according to claim 1 including a central portion.

4. A medical packaging according to claim 1 wherein the second end portions extend from a single first end portion.

5. A medical packaging according to claim 1 wherein the second end portions extend from the at least one first end portion.

6. A medical packaging according to claim 1 wherein the at least one or more first or second end portions includes one or more of:
   i. a shape corresponding to the shape of a controlling part of the single-use medical device; and
   ii. a shape corresponding to the shape of an operative part of the single-use medical device.

7. A medical packaging according to claim 1 wherein the at least one openable connection on the at least one first end portion of the body is at least one frangible connection extending on at least part of the at least one first end portion and the at least one second end portion wherein the at least one first end portion is openable with the user holding the at least one second end portion.

8. A medical packaging according to claim 1 wherein the openable connection is at a marked frangible operating line that substantially overlies the end of the key part of the device such that the frangible operating line provides an indicating line indicating the end of the key part that is not to be touched by the user and defining the key part allowable to be in direct contact with the patient.

9. A medical packaging according to claim 8 wherein the openable connection includes a plurality of marked frangible operating lines on the body of the packaging covering a particular sterile single-use medical device to be used in a plurality of different predefined uses, with each of the plurality of marked frangible operating lines substantially overlying one of a plurality of different ends of the key part of the device according to one of a plurality of the predetermined uses, such that each marked frangible operating line provides an indicating line indicating the end of the particular key part for the respective use that is not to be touched by the user and defining the particular key part allowable to be in direct contact with the patient for the respective predefined use.

10. A medical packaging according to claim 9 wherein the packaging includes a form of indication of how a medical device can be used in various ways in different medical procedures to reveal key part of the sterile single-use medical device to be used in a plurality of different predefined uses.

11. A medical packaging according to claim 1 wherein the second end portion is movable by the body being substantially flexible to allow the user to hold the one or more controlling parts and operate the one or more operative parts of the enclosed sterile single-use medical device without directly touching the device and still being substantially enclosed in the packaging body.

12. A medical packaging according to claim 11 wherein the second end portion is movable by the body being transformable to allow one or more of:
   alteration of a footprint of the single-use medical device to enable operative use of the single-use medical device while the one or more controlling parts remain substantially within the second end portion of the body;
   non-resilient alteration of the footprint of the single-use medical device;
   alteration of the volume of the body holding the single-use medical device to enable operative use of the single-use medical device while the one or more controlling parts remain substantially within the second end portion of the body; and
   non-resilient alteration of the volume of the body holding the single-use medical device.

13. A medical packaging according to claim 12 wherein the transformability is by one or more of:
   at least one part of the single second end portion transforms in a corresponding manner to the change of shape of the one or more controlling parts of the single-use medical device;
   pivoting connection of the second end portion without substantially hindering the user using the one or more controlling parts in the second end portion to control the one or more operative parts when revealed and usable directly on the patient.

14. A medical packaging according to claim 12 wherein the transformability is by one or more of:
   a sealed gusset connected to the second end portion without substantially hindering the user using the one or more controlling parts in the second end portion to control the one or more operative parts when revealed and usable directly on the patient;
a sealed concertina connection connected to the second end portion without substantially hindering the user using the one or more controlling parts in the second end portion to control the one or more operative parts when revealed and usable directly on the patient; and
a variable connected materials forming an expandible sealed connection to the second end portion without substantially hindering the user using the one or more controlling parts in the single second end portion to control the one or more operative parts when revealed and usable directly on the patient.

15. A medical packaging according to claim 1 wherein the at least one first end portion is a single first end portion for covering the one or more operative parts, and the second end portions extending from the single first end portion and for covering the one or more controlling parts
wherein the plurality of second end portions is movable relative to each other to allow movement of the one or more controlling parts while remaining in the packaging to control the one or more operative parts when revealed and usable directly on the patient.

16. A medical packaging according to claim 15 wherein the plurality of second end portions is movable relative to each other by the body being substantially flexible to allow the user to hold the one or controlling parts and operate the one or more operative parts of the enclosed sterile single-use medical device without directly touching the device and still being substantially enclosed in the packaging body.

17. A medical packaging according to claim 16 wherein the plurality of second end portions is movable relative to each other by the body being transformable to allow one or more of:
alteration of a footprint of the single-use medical device to enable operative use of the single-use medical device while the one or more controlling parts remain substantially within the plurality of second end portions of the body;
non-resilient alteration of the footprint of the single-use medical device;
alteration of the volume of the body holding the single-use medical device to enable operative use of the single-use medical device while the one or more controlling parts remain substantially within the plurality of second end portions of the body; and
non-resilient alteration of the volume of the body holding the single-use medical device.

18. A medical packaging according to claim 17 wherein the transformability is by one or more of:
at least one part of the at least one second end portion transforms in a corresponding manner to the change of shape of the one or more controlling parts of the single-use medical device; and
pivoting connection of the plurality of second end portions without substantially hindering the user using the one or more controlling parts in the plurality of second end portions to control the one or more operative parts when revealed and usable directly on the patient.

19. A medical packaging according to claim 17 wherein the transformability is by one or more of:
a sealed gusset between the plurality of second end portions without substantially hindering the user using the one or more controlling parts in the plurality of second end portions to control the one or more operative parts when revealed and usable directly on the patient;
a sealed concertina connection between the plurality of second end portions without substantially hindering the user using the one or more controlling parts in the plurality of second end portions to control the one or more operative parts when revealed and usable directly on the patient; and
a variable connected materials forming an expandible sealed connection between the plurality of second end portions without substantially hindering the user using the one or more controlling parts in the plurality of second end portions to control the one or more operative parts when revealed and usable directly on the patient.

20. A medical packaging according to claim 1 wherein the at least one first end portion is a plurality of first end portions for covering the one or more operative parts, and the at least one second end portion is a plurality of second end portions extending from the plurality of first end portions and for covering the one or more controlling parts
wherein the plurality of second end portions is movable relative to each other to allow movement of the one or more controlling parts while remaining in the packaging to control the one or more operative parts when revealed and usable directly on the patient.

21. A medical packaging according to claim 1 wherein the second end portions movable relative to each other by the body being substantially flexible to allow the user to hold the one or more controlling parts and operate the one or more operative parts of the enclosed sterile single-use medical device without directly touching the device and still being substantially enclosed in the packaging body.

22. A medical packaging according to claim 21 wherein the plurality of second end portions is movable relative to each other by the body being transformable to allow one or more of:
alteration of a footprint of the single-use medical device to enable operative use of the single-use medical device while the one or more controlling parts remain substantially within the plurality of second end portions of the body;
non-resilient alteration of the footprint of the single-use medical device;
alteration of the volume of the body holding the single-use medical device to enable operative use of the single-use medical device while the one or more controlling parts remain substantially within the plurality of second end portions of the body; and
non-resilient alteration of the volume of the body holding the single-use medical device.

23. A medical packaging according to claim 22 wherein the transformability is by one or more of:
at least one part of the at least one second end portion transforms in a corresponding manner to the change of shape of a controlling part of the single-use medical device; and
pivoting connection of the plurality of second end portions without substantially hindering the user using the one or more controlling parts in the plurality of second end portions to control the one or more operative parts when revealed and usable directly on the patient.

24. A medical packaging according to claim 1 wherein the at least part of the at least one second end portion, which is sized and shaped for substantially covering the at least one controlling part of the single-use medical device, is changeable or relatively moveable to allow controllable usage of the at least one operative part by the at least one controlling part, while retaining coverage over substantially all of the at least one controlling part of the single-use medical device.

25. A medical packaging according to claim 24 wherein the at least one second end portion is changeable by one or more of being:
   a. flexible;
   b. deformable;
   c. expandable;
   d. malleable; and
   e. compressible.

26. A medical packaging according to claim 1 wherein the plurality of single-use medical devices includes a single-use medical device selected from the categories of:
   a. fixed devices having one or more key parts;
   b. devices having one or more movable key parts;
   c. devices having one or more controlling parts; and
   d. devices having one or more movable controlling parts.

27. A medical packaging according to claim 1 wherein the plurality of single-use medical devices includes a single-use medical device from the category of single-use medical devices in which there is a fixed operative part and an opposing fixed controlling part and wherein the packaging provides a fixed shape volume enclosing the fixed single use medical device.

28. A medical packaging according to claim 1 wherein the single-use medical device is from a category of single-use medical devices in which there is a plurality of movable operative parts and an opposing plurality of movable controlling parts and wherein the packaging provides at least one first end portion for enclosing the plurality of movable operative parts and at least one second end portion for enclosing the plurality of movable controlling parts and the packaging is sized, shaped and formed of material to allow operative movable use of controlling parts and the operative parts of the single-use medical device while the controlling parts remain substantially within the packaging.

29. A medical packaging according to claim 1 wherein the single-use medical device is from a category of single-use medical devices in which there is one or more movable operative parts and one or more opposing movable controlling parts and wherein the packaging provides at least one first end portion for enclosing the one or more movable operative parts and at least one second end portion for enclosing the one or more movable controlling parts and the packaging is sized, shaped and formed of material to allow operative movable use of the one or more controlling parts and the one or more operative parts of the single-use medical device while the one or more controlling parts remain substantially within the packaging.

30. A medical packaging according to claim 1 wherein the single-use medical device is from a category of single-use medical devices in which there are one or more operative parts that are separately usable or usable in unison and the packaging includes one or more first end portions connected to one or more second end portions that extends and connects therebetween.

31. A medical packaging according to claim 1 wherein the single-use medical device is from a category of single-use medical devices in which there is an operative part and opposing controlling part and a changing shape therebetween and the packaging includes a first end portion and at least one second end portion wherein at least part of one second end portion is expandable or otherwise transformable that allows for retaining the single-use medical device in a sterile outer protection over a range of lengths or other transformations of the single-use medical device.

32. A medical packaging for holding a sterile single-use medical device, wherein the medical device has at least one operative part which in use is a key part for direct contact to a patient and further has at least one controlling part for controlling the at least one operative part, the packaging including: a body forming an enclosing volume able to hold a single-use medical device in a sterile condition, the body having at least one first end portion, at least one second end portion and at least one openable connection between the at least one first end portion and one or more of the at least one second end portion to allow the at least one first end portion to be disconnected from the at least one second end portion wherein:
   i. the at least one first end portion is sized and shaped for substantially covering one or more operative parts of the single-use medical device;
   ii. at least part of one or more of the at least one second end portion is sized and shaped for substantially covering one or more controlling parts of the single-use medical device;
   iii. the at least one openable connection is able to have the at least one first end portion displaced into an open state at time of use to allow the at least one operative part of the single-use medical device to be revealed and usable directly on the patient; and
   iv. the at least one second end portion remains substantially covering one or more controlling parts of the single-use medical device and allows the at least part of the at least one operative part to be controlled by the at least one controlling part while the at least one controlling part remains substantially within the at least one second end portion;
   wherein the openable connection is at a marked frangible operating line that substantially overlies the end of the key part of the device such that the frangible operating line provides an indicating line indicating the end of the key part that is not to be touched by the user and defining the key part allowable to be in direct contact with the patient;
   wherein the openable connection includes a plurality of marked frangible operating lines on the body of the packaging covering a particular sterile single-use medical device to be used in a plurality of different predefined uses, with each of the plurality of marked frangible operating lines substantially overlying one of a plurality of different ends of the key part of the device according to one of a plurality of the predetermined uses, such that each marked frangible operating line provides an indicating line indicating the end of the particular key part for the respective use that is not to be touched by the user and defining the particular key part allowable to be in direct contact with the patient for the respective predefined use;
   wherein the packaging includes a form of indication of how a medical device can be used in various ways in different medical procedures to reveal key part of the sterile single-use medical device to be used in a plurality of different predefined uses;
   wherein the form of indication is a colour code in which the first end portion extending to the different frangible operating lines of the plurality of marked frangible operating lines is differently coloured such that a first type of medical procedure for the particular sterile single-use medical device is coloured a first colour and the user knows to remove the first end portion of the first colour revealing the required shallow key part forming the operative part up to the line of the relevant frangible operating line and wherein other medical procedures requiring different key parts are identified by different colours to allow the appropriate first end portion up to the appropriate frangible operating line to be removed and reveal the appropriate key part of the sterile single-use device.

33. A medical packaging according to claim 32 wherein the at least one first end portion is a single first end portion for covering the one or more operative parts, and the at least one second end portion is a single second end portion extending from the single first end portion and for covering one or more controlling parts
wherein the single second end portion is movable to allow movement of the one or more controlling parts while remaining in the packaging to control the one or more operative parts when revealed and usable directly on the patient.

34. A medical packaging according to claim 32
wherein the at least one first end portion is a plurality of first end portions for covering the one or more operative parts, and the at least one second end portion is a single second end portion extending from the plurality of first end portions and for covering the one or more controlling parts wherein the single second end portion is movable to allow movement of the one or more controlling parts while remaining in the packaging to control the one or more operative parts when revealed and usable directly on the patient.

35. A medical packaging according to claim 32 is for covering a scalpel and the openable connection of packaging includes a plurality of marked frangible operating lines on the body of the packaging indicating the respective use that is not to be touched by the user and defining the particular key part allowable to be in direct contact with the patient for the respective predefined use.

36. A medical packaging according to claim 32 is for covering tweezers and includes an enclosing body of a plurality of first end portions forming an enclosing sealed volume when connected with a bifurcated second end portion and the openable connection of packaging includes one or more marked frangible operating lines on the body of the packaging indicating the respective use that is not to be touched by the user and defining the particular key part allowable to be in direct contact with the patient for the respective predefined use.

37. A medical packaging according to claim 32 is for covering a syringe having a plunger, a barrel and an operative dispensing end and includes a non-resilient enclosing body substantially following the shape of the syringe having:
at least one first end portion attached to at least one second end portion and
at least one frangible connection over the operative dispensing end which allows operatively effective filling and dispensing function of the syringe
and the at least one second end portion including a transformable part able to follow the change of volume of the syringe by the insertion and retraction of the plunger in the barrel with the transformable part being in the form of one or more of:
a) a sealed gusset connected to the at least one second end portion;
b) a sealed concertina connection connected to the at least one second end portion; and
c) a variable connected material forming an expandable sealed connection to the at least one second end portion;
wherein the user is not substantially hindered using the one or more controlling parts in the at least one second end portion to control the one or more operative parts when revealed and usable directly on the patient
and wherein the covering of the one or more controlling parts including the plunger and barrel of the syringe and the one or more openable frangible connections indicating the respective use that is not to be touched by the user and defining the particular key part allowable to be in direct contact with the patient for the respective predefined use.

38. A medical packaging for holding a sterile single-use medical device, wherein the medical device has at least one operative part which in use is a key part for direct contact to a patient and further has at least one controlling part for controlling the at least one operative part, the packaging including: a body forming an enclosing volume able to hold a single-use medical device in a sterile condition, the body having at least one first end portion, at least one second end portion and at least one openable connection between the at least one first end portion and one or more of the at least one second end portion to allow the at least one first end portion to be disconnected from the at least one second end portion wherein:
i. the at least one first end portion is sized and shaped for substantially covering one or more operative parts of the single-use medical device;
ii. at least part of one or more of the at least one second end portion is sized and shaped for substantially covering one or more controlling parts of the single-use medical device;
iii. the at least one openable connection is able to have the at least one first end portion displaced into an open state at time of use to allow the at least one operative part of the single-use medical device to be revealed and usable directly on the patient; and
iv. the at least one second end portion remains substantially covering one or more controlling parts of the single-use medical device and allows the at least part of the at least one operative part to be controlled by the at least one controlling part while the at least one controlling part remains substantially within the at least one second end portion,
wherein the at least one second end portion is a plurality of second end portions movable relative to each other by the body being substantially flexible to allow the user to hold the one or more controlling parts and operate the one or more operative parts of the enclosed sterile single-use medical device without directly touching the device and still being substantially enclosed in the packaging body,
wherein the plurality of second end portions is movable relative to each other by the body being transformable to allow one or more of:
alteration of the footprint of the single-use medical device to enable operative use of the single-use medical device while the one or more controlling parts remain substantially within the plurality of second end portions of the body,
non-resilient alteration of the footprint of the single-use medical device,
alteration of the volume of the body holding the single-use medical device to enable operative use of the single-use medical device while the one or more controlling parts remain substantially within the plurality of second end portions of the body, and non-resilient alteration of the volume of the body holding the single-use medical device
wherein the transformability is by one or more of:
a sealed gusset between the plurality of second end portions without substantially hindering the user using the one or more controlling parts in the plurality of second end portions to control the one or more operative parts when revealed and usable directly on the patient;
a sealed concertina connection between the plurality of second end portions without substantially hindering the user using the one or more controlling parts in the plurality of second end portions to control the one or more operative parts when revealed and usable directly on the patient; and
a variable connected materials forming an expandable sealed connection between the plurality of second end portions without substantially hindering the user using the one or more controlling parts in the plurality of second end portions to control the one or more operative parts when revealed and usable directly on the patient.

39. A medical packaging for holding a sterile single-use medical device, wherein the medical device has at least one operative part which in use is a key part for direct contact to a patient and further has at least one controlling part for controlling the at least one operative part, the packaging including: a body forming an enclosing volume able to hold a single-use medical device in a sterile condition, the body having at least one first end portion, at least one second end portion and at least one openable connection between the at least one first end portion and one or more of the at least one second end portion to allow the at least one first end portion to be disconnected from the at least one second end portion wherein:
  i. the at least one first end portion is sized and shaped for substantially covering one or more operative parts of the single-use medical device;
  ii. at least part of one or more of the at least one second end portion is sized and shaped for substantially covering one or more controlling parts of the single-use medical device;
  iii. the at least one openable connection is able to have the at least one first end portion displaced into an open state at time of use to allow the at least one operative part of the single-use medical device to be revealed and usable directly on the patient; and
  iv. the at least one second end portion remains substantially covering one or more controlling parts of the single-use medical device and allows the at least part of the at least one operative part to be controlled by the at least one controlling part while the at least one controlling part remains substantially within the at least one second end portion
    wherein the medical packaging is for covering a suture scissors and the openable connection of packaging includes a plurality of marked frangible operating lines on the body of the packaging indicating the respective use that is not to be touched by the user and defining the particular key part allowable to be in direct contact with the patient for the respective predefined use.

40. A medical packaging according to claim 39 wherein the packaging is transformable and the transformability is by one or more of:
at least one part of the single second end portion transforms in a corresponding manner to the change of shape of a controlling part of the single-use medical device; and
pivoting connection of the second end portion without substantially hindering the user using the one or more controlling parts in the second end portion to control the one or more operative parts when revealed and usable directly on the patient.

41. A medical packaging according to claim 39 wherein the packaging is transformable and the transformability is by one or more of:
a sealed gusset connected to the second end portion without substantially hindering the user using the one or more controlling parts in the second end portion to control the one or more operative parts when revealed and usable directly on the patient;
a sealed concertina connection connected to the second end portion without substantially hindering the user using the one or more controlling parts in the second end portion to control the one or more operative parts when revealed and usable directly on the patient; and
a variable connected materials forming an expandable sealed connection to the second end portion without substantially hindering the user using the one or more controlling parts in the single second end portion to control the one or more operative parts when revealed and usable directly on the patient.

42. A medical packaging for holding a sterile single-use medical device, wherein the medical device has at least one operative part which in use is a key part for direct contact to a patient and further has at least one controlling part for controlling the at least one operative part, the packaging including: a body forming an enclosing volume able to hold a single-use medical device in a sterile condition, the body having at least one first end portion, at least one second end portion and at least one openable connection between the at least one first end portion and one or more of the at least one second end portion to allow the at least one first end portion to be disconnected from the at least one second end portion wherein:
  i. the at least one first end portion is sized and shaped for substantially covering one or more operative parts of the single-use medical device;
  ii. at least part of one or more of the at least one second end portion is sized and shaped for substantially covering one or more controlling parts of the single-use medical device;
  iii the at least one openable connection is able to have the at least one first end portion displaced into an open state at time of use to allow the at least one operative part of the single-use medical device to be revealed and usable directly on the patient; and
  iv. the at least one second end portion remains substantially covering one or more controlling parts of the single-use medical device and allows the at least part of the at least one operative part to be controlled by the at least one controlling part while the at least one controlling part remains substantially within the at least one second end portion;
    wherein the medical packaging is for covering a scissors and includes an enclosing body of at least one first end portion attached to a bifurcated at least one second end portion which allows operatively effective function of the scissors while the at least one controlling part including finger location shapes remains substantially within the at least one second end portion, wherein at least part of the one or more second end portions is sized and shaped for substantially following and covering a controlling part including the finger location shapes of the scissors and the openable connection of packaging includes a marked frangible operating line on the body of the packaging indicating the respective use that is not to be touched by the user and defining the key part allowable to be in direct contact with the patient, wherein the one or more second end portions is movable by the body being transformable to allow one or more of:

alteration of the footprint of the scissors to enable operative use of the scissors while at least part of the one or more controlling parts remains substantially within the at least one second end portion of the body;

non-resilient alteration of the footprint of the scissors;

alteration of the volume of the body holding the scissors to enable operative use of the scissors while at least part of the one or more controlling parts remain substantially within the at least one second end portion of the body; and non-resilient alteration of the volume of the body holding the scissors and wherein the transformability is provided by one or more of:

a) a sealed gusset connected to the at least one second end portion;

b) a sealed concertina connection connected to the at least one second end portion; and c) a variable connected material forming an expandible sealed connection to the at least one second end portion, and wherein the user is not substantially hindered using the one or more controlling parts in the at least one second end portion to control the one or more operative parts when revealed and usable directly on the patient.

* * * * *